(12) United States Patent
Kreuder et al.

(10) Patent No.: US 6,187,224 B1
(45) Date of Patent: Feb. 13, 2001

(54) OPTICAL BRIGHTENING AGENT

(75) Inventors: Willi Kreuder, Mainz; Josef Salbeck, Kelkheim, both of (DE)

(73) Assignee: Axiva GmbH (DE)

( * ) Notice: Under 35 U.S.C. 154(b), the term of this patent shall be extended for 0 days.

(21) Appl. No.: 09/284,621

(22) PCT Filed: Nov. 22, 1995

(86) PCT No.: PCT/EP97/05888

§ 371 Date: Jul. 6, 1999

§ 102(e) Date: Jul. 6, 1999

(87) PCT Pub. No.: WO98/18996

PCT Pub. Date: May 7, 1998

(30) Foreign Application Priority Data

Oct. 31, 1996 (DE) .............................................. 196 45 063

(51) Int. Cl.$^7$ .............................. C09K 11/06; F21V 9/04
(52) U.S. Cl. ...................................... 252/301.21; 252/589
(58) Field of Search ............................... 252/589, 301.21

(56) References Cited

U.S. PATENT DOCUMENTS 5,354,511 * 10/1994 Wu et al. ............................. 252/582
5,840,217 11/1998 Lupo et al. ........................... 252/583

FOREIGN PATENT DOCUMENTS

| 44 42 050 | 11/1994 | (DE) . |
| 676 461 | 3/1995 | (EP) . |
| 96/17035 | 6/1996 | (WO) . |

* cited by examiner

*Primary Examiner*—C. H. Kelly
(74) *Attorney, Agent, or Firm*—Connolly Bove Lodge & Hutz LLP

(57) ABSTRACT

An optical brightener comprising one or more spiro compounds of the formula (I),

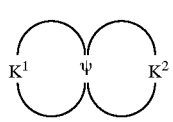

(I)

where $K^1$ and $K^2$, which are identical or different, are conjugated systems, and ψ is C, Si, Ge, Sn or Pb, is notable for high fluorescence quantum yields and a high temperature stability.

13 Claims, No Drawings

OPTICAL BRIGHTENING AGENT

DESCRIPTION

According to Römpps Chemie Lexikon (Römpp Hermann [original author]; Falbe, Jürgen [editor]; Chemie Lexikon, Georg Thieme Verlag, Stuttgart 1991) optical brighteners are chemical compounds which remove graying and yellowing from textiles, paper, plastics etc.; like dyes, they are drawn out of the liquor onto the fiber or are incorporated into the material in question, and bring about brightening and at the same time simulate a bleaching action by converting (invisible) ultraviolet radiation into (visible) light of longer wavelength. The ultraviolet light absorbed from the sunlight is reradiated as weak bluish fluorescence, i.e. in the complementary color of yellowing. These organic luminescent pigments (fluorescent dyes) thus act like optical transformers.

Optical brighteners known from the prior art comprise, for example, derivatives of 4,4'-diamino-2,2'-stilbenedisulfonic acid (flavonic acid), 4,4'-distyrylbiphenylene, methylumbelliferone, coumarin, dihydroquinolinone, 1,3-diarylpyrazoline, naphthalimide, benzoxazole, benzisoxazole and benzimidazole systems linked via CH=CH bonds, or pyrene derivatives substituted by heterocycles.

Although the known optical brighteners achieve very good results, there is a continuing need for novel improved systems since the requirements, for example as regards brightness, fastness toward sunlight, washing, ironing, additives simultaneously used, environmental compatibility and cost efficiency, are also continually increasing.

Surprisingly, it has now been found that organic spiro compounds which comprise a conjugated system are particularly suitable for use as optical brighteners.

Spiro compounds have at least one tetravalent spiro atom which links two ring systems together. This is explained in the Handbook of Chemistry and Physics, 62nd ed. (1981–2), p. C-23 to 25.

The invention thus provides an optical brightener comprising one or more spiro compounds of the formula (I),

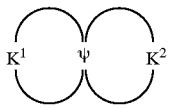

(I)

where $K^1$ and $K^2$, independently of one another, are conjugated systems, and ψ is C, Si, Ge, Sn, Pb, preferably C or Si, particularly preferably C.

Compared with conventional optical brighteners, the compounds used according to the invention have exceptional temperature stability. This is evident, for example, from the fact that the emission maximum of the compounds after heating decreases only slightly, and in some cases not at all, and that in the case of many of these compounds, even an increase in the emission maximum after heating is observed. This makes it possible to brighten those polymeric materials in which the brightener can only be incorporated into the polymeric material in the melt process (in particular industrial polymeric materials, e.g. aramid fibers). The high temperatures required for this purpose lead, in the case of the brighteners customary hitherto, to their thermal decomposition. In the production of conventional fibers, the wet spinning process can here be replaced by the melt process, which is solvent-free and therefore to be preferred for ecological reasons.

Compared with brighteners known hitherto, as well as thermal stability, improved photostability, preferably in the case of carbocyclic aromatic systems, is also achieved.

Because of the relatively high thermal and photochemical stability compared with prior art brighteners, brightening is also possible in fields of application which have hitherto been excluded. For example, these compounds can, in principle, also be used for brightening geotextiles and, because the brightener molecules have a low tendency to migrate, packaging materials.

The fluorescence quantum yield of the spiro compounds in solution and in the solid matrix can be greater than 95%. As a result, lower brightener concentrations are required for the same or, in most cases, improved brightening effect, which is advantageous both for cost reasons and for ecological reasons. Aggregation phenomena, often a problem with conventional brighteners, do not arise in the case of spiro compounds because of their structure. As a result, a favorable and, for some areas of application, necessary molecularly disperse distribution is achieved. The low tendency toward aggregation can be further utilized to achieve very high brightener concentrations, up to the pure, preferably amorphous, compound, for example in the form of a film, but nevertheless to obtain a high fluorescence quantum yield, i.e. concentration quenching does not take place.

Furthermore, these compounds are notable for high temperature stability with regard to color stability and fluorescence quantum yield. This means that the emission maximum in the range from 380 to 750 nm, measured at room temperature, decreases by no greater than 25%, relative to the initial state, after the material, applied in a thickness of no greater than 1 μm to a quartz substrate, has been heated to 250° C. in an inert atmosphere at a pressure no greater than 1 mbar for 30 min.

The reduction in the emission maximum is preferably no greater than 20%, particularly preferably 15%, relative to the initial state before thermal treatment.

The invention thus further provides an optical brightener a) which has a fluorescence quantum yield of ≧40%, preferably ≧50%, particularly preferably ≧60% in the, preferably amorphous, solid, and b) the emission maximum in the range from 380 to 750 nm, measured at room temperature, decreases by no greater than 25%, relative to the initial state, after the material, applied in a thickness of no greater than 1 μm to a quartz substrate, has been heated to 250° C. in an inert atmosphere at a pressure no greater than 1 mbar for 30 min.

Using the Spiro compounds, it is also possible to adjust the color shade by varying the substituents on the spirobifluorene parent substance.

For some applications, for example as effective, thin UV filters, it is also advantageous if the spiro compounds used according to the invention can be prepared amorphously. For filter applications it is advantageous if the compounds have very high extinction coefficients in the UV region, preferably between 250 and 380 nm, and can be prepared in very high brightener concentrations, up to the pure film (100%), as amorphous, thin films (for example by spin coating or sublimation).

The term amorphous is used to describe the state of solids whose molecular building blocks are arranged not in crystal lattices, but irregularly. Unlike a crystal where there is short-range order (i.e. constant distances to the nearest neighboring atoms) and long-range order (regular repetition of a base lattice) between the atoms, the amorphous state has only short-range order. The amorphous material has no physically distinguishable direction; it is isotropic. All amorphous substances strive, to varying degrees, to achieve the more energetically favorable crystalline state. In the diffraction of X-rays, electron rays and neutron rays, amorphous solids do not give sharp interference rings, as in a crystal, but only diffuse interference rings at low diffraction angles (halos).

The amorphous state is thus clearly distinguishable from the crystalline, liquid or liquid-crystalline state.

Compared with many known systems, the spiro compounds according to the invention are also readily soluble, particularly in polar solvents, in particular dichloromethane and chloroform (>30 g/l), meaning that spin coating and film formation inter alia are possible.

Processability from aqueous systems is achieved by substitution of the spiro compounds for strongly polar groups, such as carboxylic acid, carboxylate, sulfonic acid, sulfonate and quaternary ammonium groups.

The emission properties of the compounds used according to the invention can be adjusted over the entire region of the visible spectrum through the choice of suitable substituents. Furthermore, the covalently bonded arrangement of the two parts of the spiro compound permits a molecular structure such that in both halves of the molecule certain properties can be established independently of one another, e.g. an extension of the absorption region into the longwave UV.

Preferred compounds of the formula (I) are the 9,9'-spiro compounds of the formula (II).

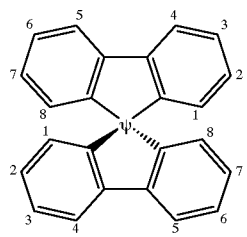

(II)

where ψ is as defined above and the benzo groups can, independently of one another, be substituted and/or fused.

Particular preference is given to spirobifluorenes of the formula (III),

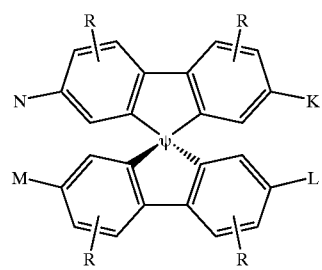

(III)

where ψ is as defined above and the other symbols and indices are as defined below:

K, L, M, N are identical or different and are a group of the formulae

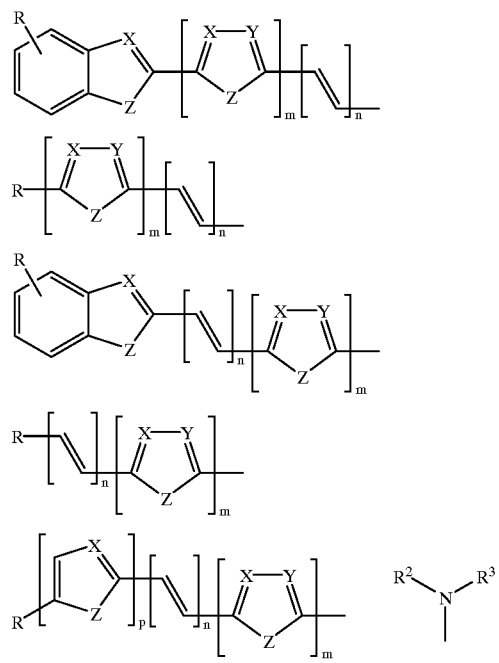

R is identical or different and is as defined for K, L, M, N or is —H, a linear or branched alkyl, alkoxy or carboalkoxy group having from 1 to 22, preferably from 1 to 15, particularly preferably from 1 to 12, carbon atoms, —CN, —NO$_2$, —NR$^2$R$^3$, —$^+$NR$^2$R$^3$R$^4$, NOR$^2$R$^3$, —Ar or —O—Ar, preferably —SO$_2$CH$_3$, —CF$_3$, halogen, —SO$_3$H, —SO$_3$Na(K), —PO(OC$_2$H$_5$)$_2$, —CH$_3$OSO$_3$—, —N(CH$_3$)$_3^+$, —O—(CH$_2$)$_2$)—N$^+$(CH$_3$)(C$_2$H$_5$)$_2$;

Ar is phenyl, biphenyl, 1-naphthyl, 2-naphthyl, 2-thienyl, 2-furanyl, where each of these groups can carry one or two radicals R, m, n, p are 0, 1, 2, 3, 4, 5, where n is preferably 0;

X, Y are identical or different and are CR or nitrogen;

Z is —O—, —S—, —NR—, —CRR$^1$—, —CH=CH—, —CH=N—;

R$^1$ is as defined for R;

R$^2$, R$^3$, R$^4$ are identical or different and are H, a linear or branched alkyl group having from 1 to 22 carbon atoms, —Ar, 3-methylphenyl.

Preferred compounds of the formula (III) are those of the formula (IIIa)–(IIIg):

IIIa) K=L=M=N and is a group of the formula:
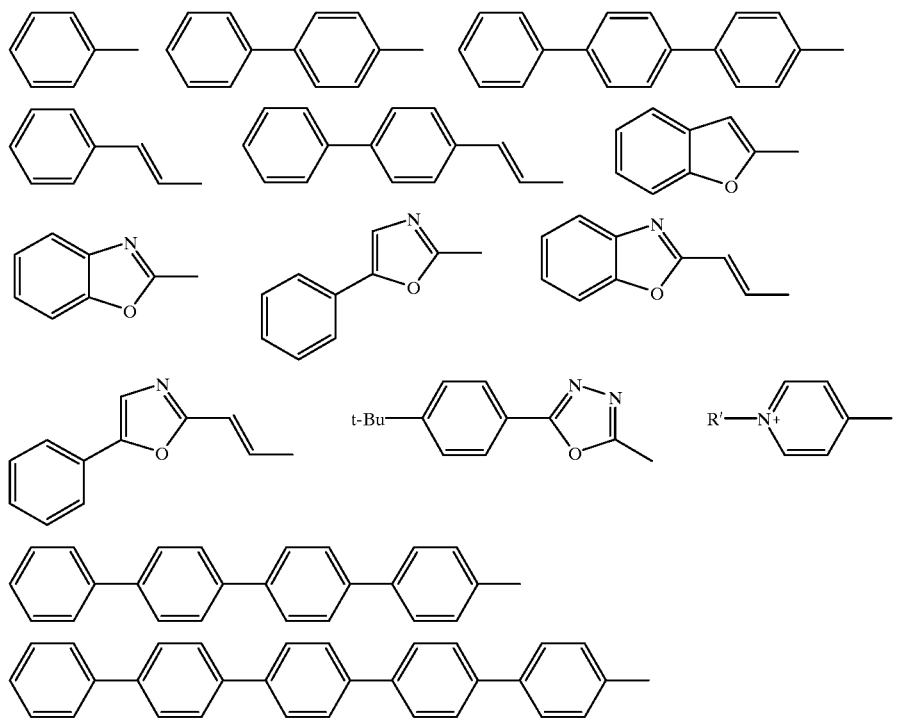
R'=C$_1$–C$_{22}$-alkyl, C$_2$H$_4$SO$_3^-$
IIIb) K=M=H and N=L and is a group of the formula:
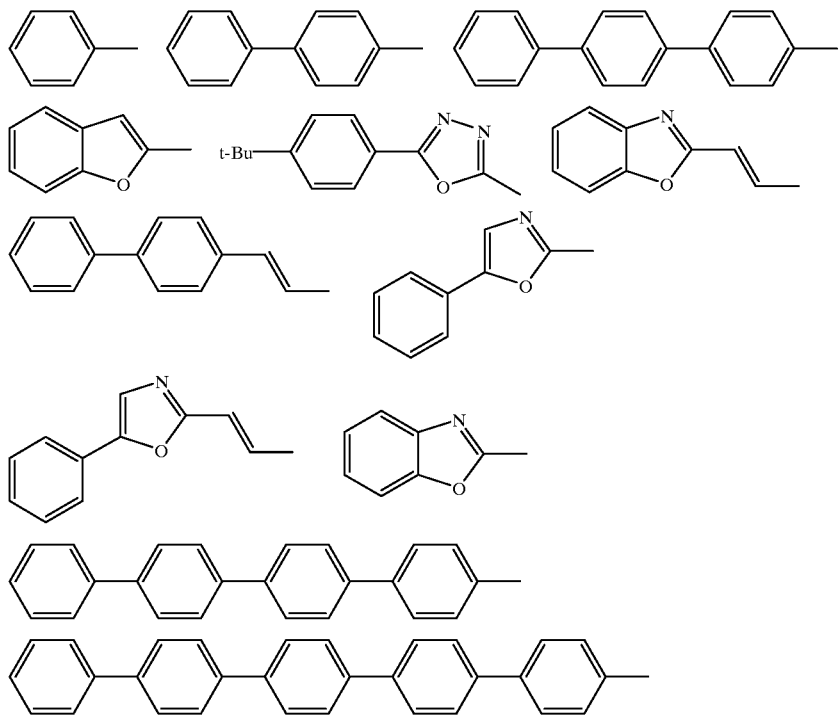

IIIc) K=M and is a group of the formula:
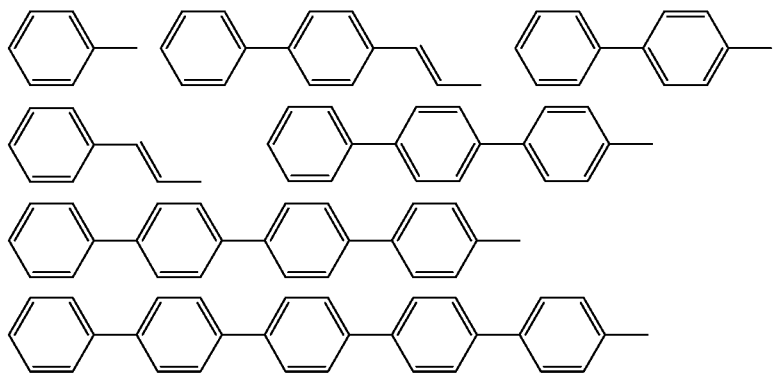
R'=C$_1$–C$_{22}$-alkyl, C$_2$H$_4$SO$_3^-$ and N=L and is a group of the formula:
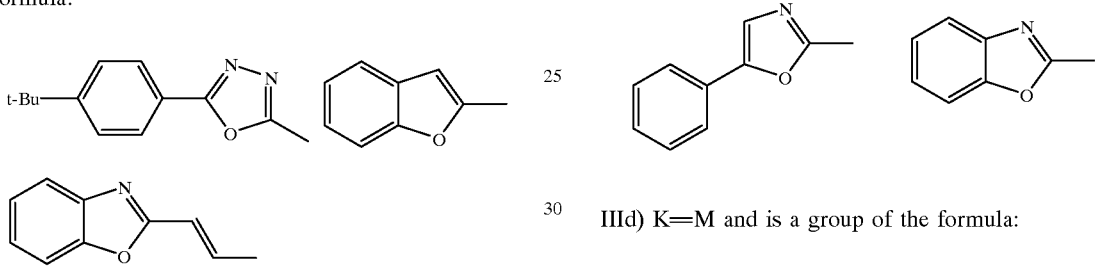
IIId) K=M and is a group of the formula:
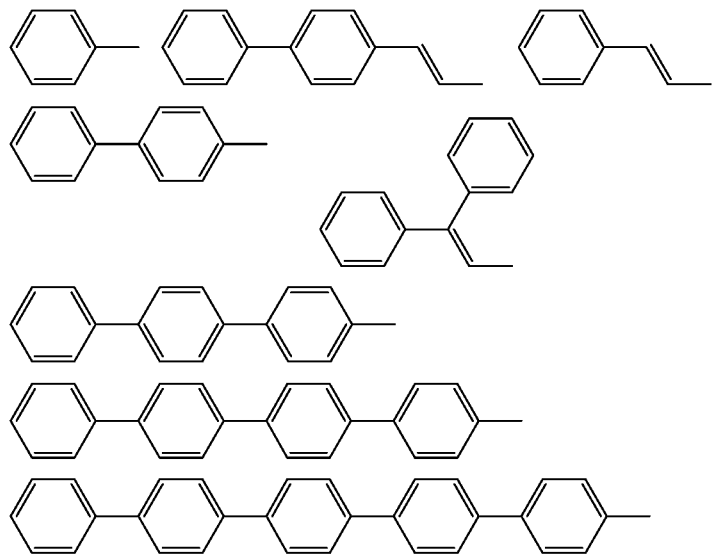
and N=L and is a group of the formula:
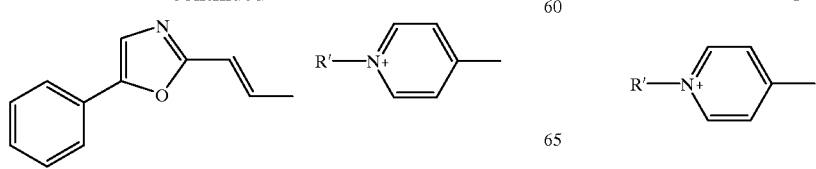
R'=C$_1$–C$_{22}$-alkyl, C$_2$H$_4$SO$_3^-$ IIIe) K=L=H and M=N and is a group of the formula:
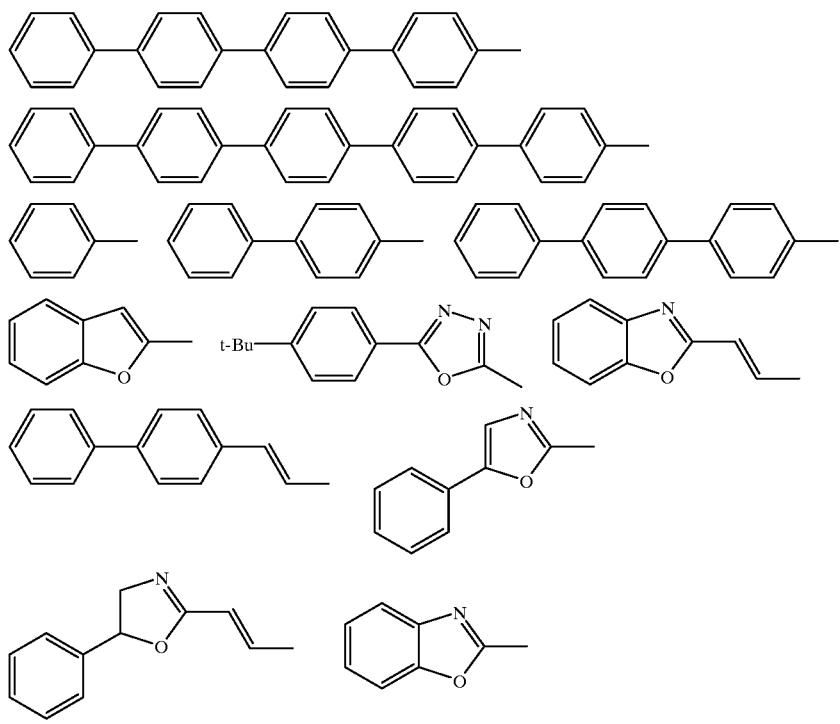
IIIf) K=M and is a group of the formula:
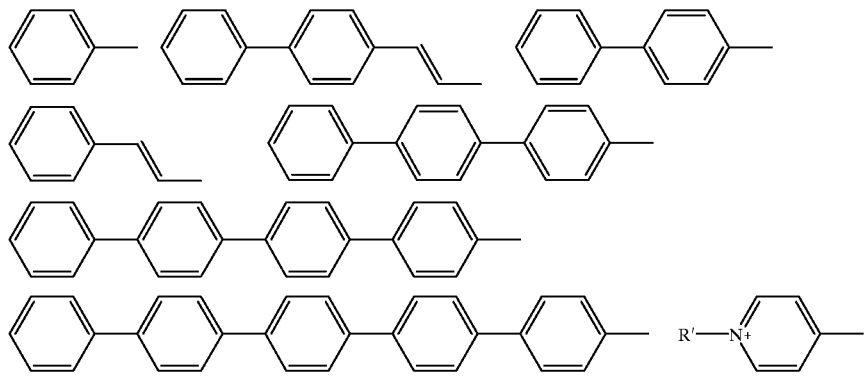
R'=C$_1$–C$_{22}$-alkyl, C$_2$H$_4$SO$_3^-$
and M=N and is a group of the formula:
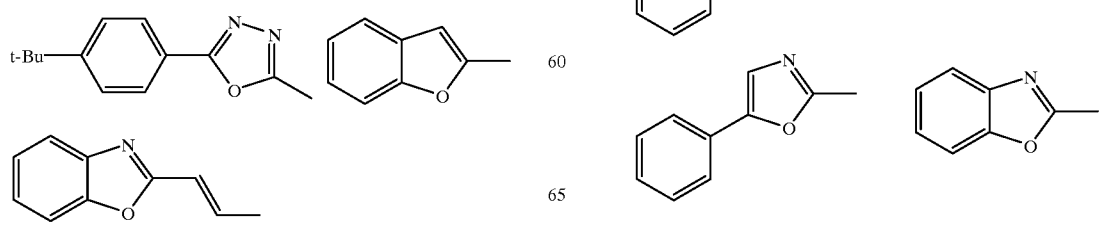
-continued IIIg) K=L and is a group of the formula:
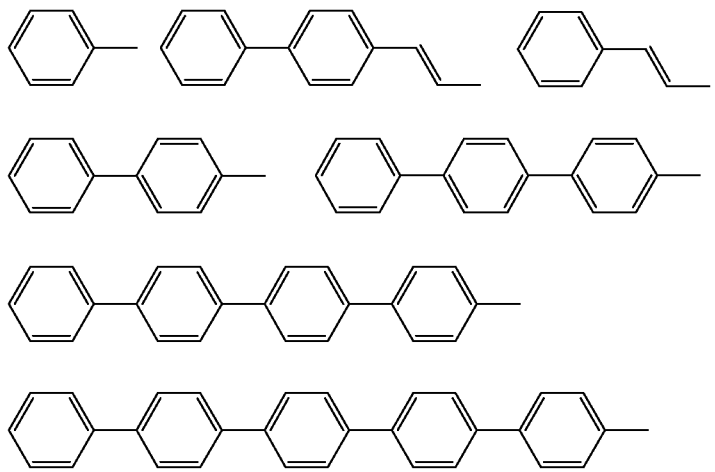
and M=N and is a group of the formula:
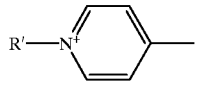
R'=C$_1$–C$_{22}$-alkyl, C$_2$H$_4$SO$_3^-$
Particularly preferred compounds of the formula (III) are those of the formulae (IIIaa) to (IIIdb):
(IIIaa) K=L=M=N and is a group of the formula:
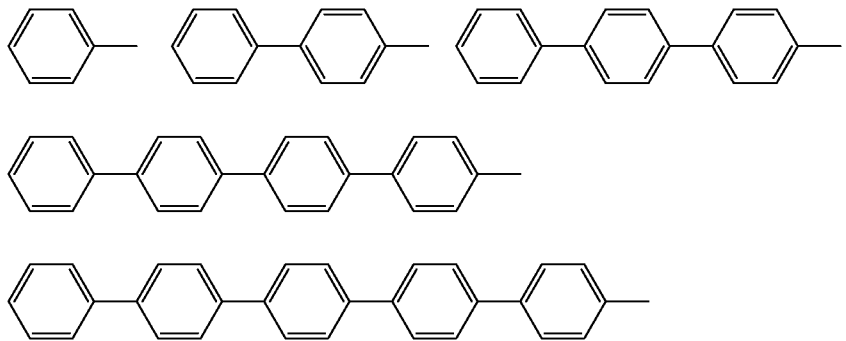
(IIIba) K=M=H and N=L and is a group of the formula:
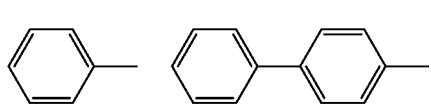
-continued
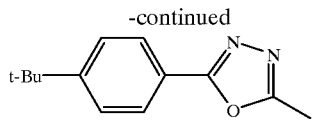
(IIIca) K=M and is a group of the formula:
and N=L and is:
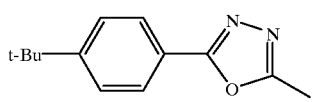

(IIIda) K=M and is a group of the formula:
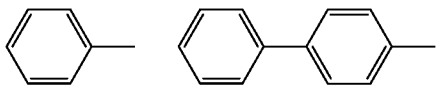
(IIIcb) K=L and is a group of the formula:
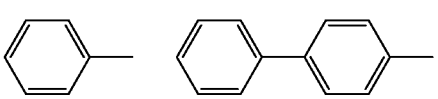
(IIIab) K=L=M=N and is a group of the formula:
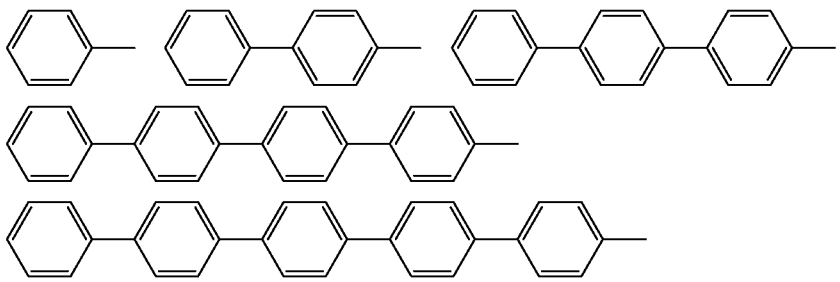
(IIIbb) K=L=H and M=N and is a group of the formula:
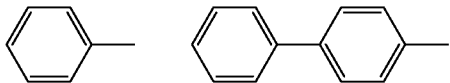
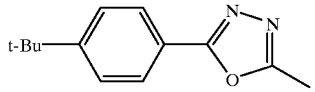
and M=N and is:
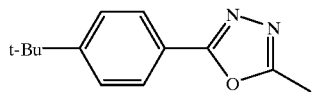
(IIIdb) K=L and is a group of the formula:
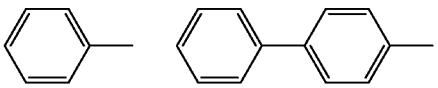
and M=N and is a group of the formula:
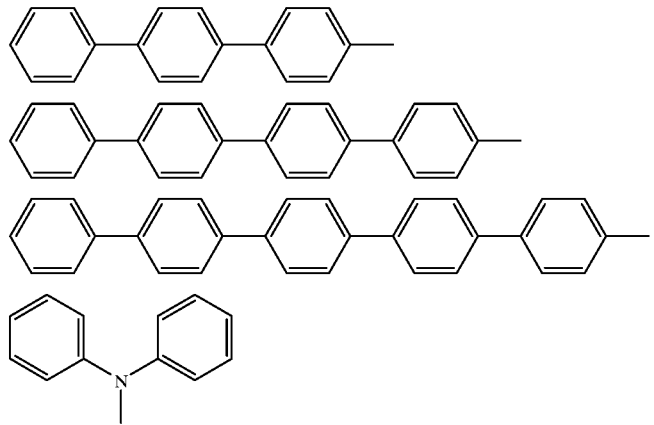

Very particularly preferred Spiro compounds are those of the formula (IV),

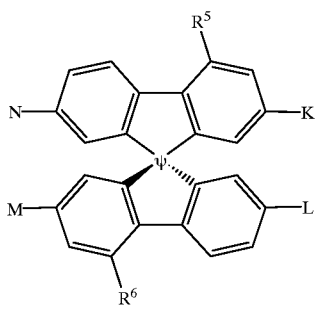

(IV)

where the symbols are defined as follows:

K, L, M, N, R⁵, R⁶ are identical or different and are one of the groups G1 to G11;

and $R^5$, $R^6$ can also be identical or different and can be hydrogen or a linear or branched alkyl, alkyloxy or ester group having from 1 to 22 carbon atoms, —CN or —NO$_2$.

Particularly preferred spiro compounds of the formula (IV) are the compounds listed in Table 1, in which the abbreviations G1 to G11 are as defined in formula (IV).

TABLE 1

| Spiro compounds of the formula (IV) $R^5 = R^6 =$ hydrogen | | | | |
|---|---|---|---|---|
| Compound | K | L | M | N |
| Spiro-1 | G1 | G1 | G3 | G3 |
| Spiro-2 | G1 | G1 | G4 | G4 |
| Spiro-3 | G1 | G1 | G5 | G5 |
| Spiro-4 | G1 | G1 | G6 | G6 |
| Spiro-5 | G1 | G1 | G7 | G7 |
| Spiro-6 | G1 | G1 | G8 | G8 |
| Spiro-7 | G1 | G1 | G9 | G9 |
| Spiro-8 | G1 | G1 | G10 | G10 |

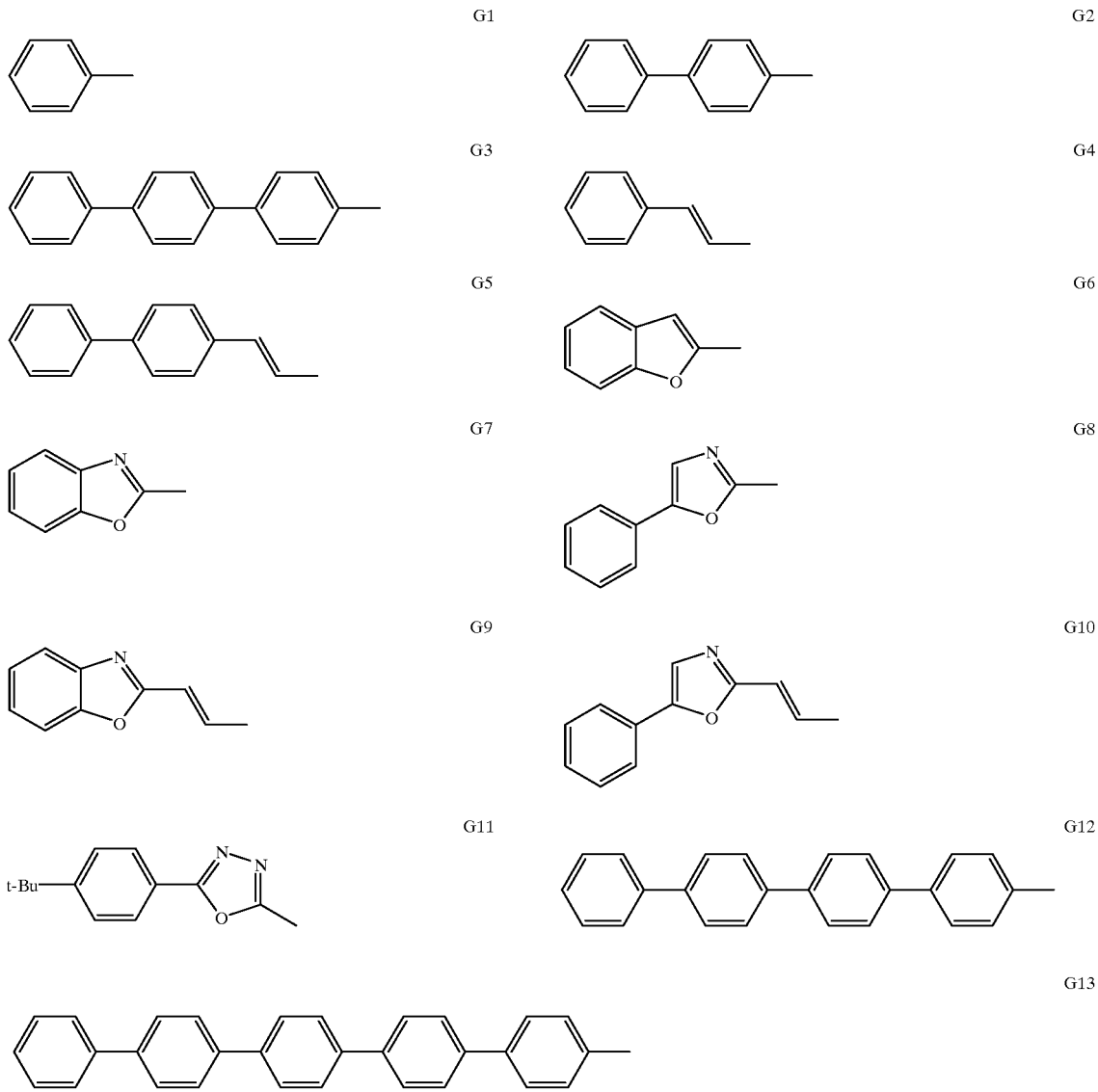

TABLE 1-continued

| | Spiro compounds of the formula (IV) $R^5 = R^6$ = hydrogen | | | |
|---|---|---|---|---|
| Compound | K | L | M | N |
| Spiro-9 | G1 | G1 | G11 | G11 |
| Spiro-10 | G2 | G2 | G2 | G2 |
| Spiro-11 | G2 | G2 | G3 | G3 |
| Spiro-12 | G12 | G12 | G12 | G12 |
| Spiro-13 | G13 | G13 | G13 | G13 |

Preference is also given to spiro compounds of the formula (V),

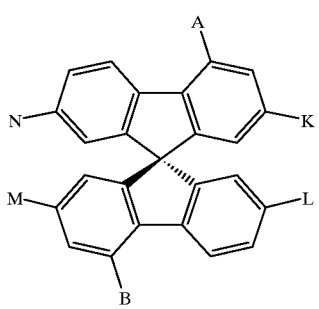

(V)

where A, B, K, L, M, N are identical or different and are as defined for K, L, M and N for the formula (III).

Preference is given to compounds of the formula (V) in which K, L, M, N, A and B are the groups G1 to G13 already listed above.

Especially preferred spiro compounds of the formula (V) are 2,2',4,4',7,7'-hexakis(biphenylyl)-9,9'-spirobifluorene,
2,2',4,4',7,7'-hexakis(terphenylyl)-9,9'-spirobifluorene
2,2',4,4',7,7'-hexakis(quaterphenylyl)-9,9'-spirobifluorene
2,2',4,4',7,7'-hexakis(pentaphenylyl)-9,9'-spirobifluorene The spiro compounds used according to the invention are prepared by methods known per se from the literature, as are described in standard works on organic synthesis, e.g. Houben-Weyl, Methoden der Organischen Chemie, Georg-Thieme-Verlag, Stuttgart and in the appropriate volumes of the series "The Chemistry of Heterocyclic Compounds" by A. Weissberger and E. C. Taylor (editors).

The preparation is carried out under reaction conditions which are known and suitable for said reactions. Use can also be made here of variants which are known per se and are not mentioned in more detail here.

Carbospiro compounds (ψ=C)

Compounds of the formula (IIIa) are obtained, for example, starting from 9,9'-spirobifluorene, the synthesis for which is described, for example, by R. G. Clarkson, M. Gomberg, J.Am.Chem.Soc. 52 (1930) 2881.

Compounds of the formula (IIIa) can be prepared, for example, starting from a tetrahalogenation in the 2,2',7,7' positions of 9,9'-spirobifluorene and a subsequent substitution reaction (see, for example, U.S. Pat. No. 5,026,894) or via a tetraacetylation of the 2,2',7,7' positions of 9,9'-spirobifluorene with subsequent C—C linkage after converting the acetyl groups into aldehyde groups, or constructing a heterocycle after converting the acetyl groups into carboxylic acid groups.

Compounds of the formula (IIIb) can be prepared, for example, by a method similar to those of the formula IIIa, the stoichiometric ratios in the reaction being chosen such that the 2,2' or 7,7' positions are functionalized (see, for example, J. H. Weisburger, E. K. Weisburger, F. E. Ray, J. Am. Chem. Soc. 72 (1959) 4253; F. K. Sutcliffe, H. M. Shahidi, D. Paterson, J. Soc. Dyers Colour 94 (1978) 306 and G. Haas, V. Prelog, Helv. Chim. Acta 52 (1969) 1202).

Compounds of the formula (IIIc) can be prepared, for example, via a dibromination in the 2,2' position and subsequent diacetylation in the 7,7' position of 9,9'-spirobifluorene and subsequent reaction by a similar method to that for the compounds IIIa.

Compounds of the formulae (IIIe)–(IIIg) can be prepared, for example, by choosing suitably substituted starting compounds for the construction of the spirobifluorene, e.g. 2,7-dibromospirobifluorene can be obtained from 2,7-dibromofluorenone and 2,7-dicarbethoxy-9,9-spirobifluorene using 2,7-dicarbethoxyfluorenone. The free 2',7' positions on the spirobifluorene can then be further substituted independently.

For the synthesis of the K, L, M, N groups, reference may be made, for example, to DE-A 23 44 732, 24 50 088, 24 29 093, 25 02 904, 26 36 684, 27 01 591 and 27 52 975 for compounds containing 1,4-phenylene groups; DE-A 26 41 724 for compounds containing pyrimidin-2,5-diyl groups; DE-A 40 26 223 and EP-A 03 91 203 for compounds containing pyridin-2,5-diyl groups;

DE-A 32 31 462 for compounds containing pyridazin-3,6-diyl groups; N. Miyaura, T. Yanagi and A. Suzuki in Synthetic Communications 11 (1981) 513 to 519, DE-A-3 930 663, M. J. Sharp, W. Cheng, V. Snieckus in Tetrahedron Letters 28 (1987), 5093; G. W. Gray in J. Chem. Soc. Perkin Trans 11 (1989) 2041 and Mol. Cryst. Liq. Cryst. 172 (1989) 165, Mol. Cryst. Liq. Cryst. 204 (1991) 43 and 91; EP-A 0 449 015; WO 89/12039; WO 89/03821; EP-A 0 354 434 for the direct linking of aromatics and heteroaromatics.

The preparation of disubstituted pyridines, disubstituted pyrazines, disubstituted pyrimidines and disubstituted pyridazines is given, for example, in the appropriate volumes of the series "The Chemistry of Heterocyclic Compounds" by A. Weissberger and E. C. Taylor (editors).

Heterospiro compounds (ψ=C)

The preparation is carried out under reaction conditions which are known and suitable for said reactions. Use can here also be made of variants which are known per se and are not mentioned in more detail here.

Compounds of the formula (III) are obtained, for example, starting from bis[biphenyl-2,2'-diyl]silane (=9,9'-spirobi(9H-)-silafluorene) (V), the synthesis of which is described, for example, by H. Gilman, R. D. Gorsich, J. Am. Chem. Soc. 1958, 80, 3243.

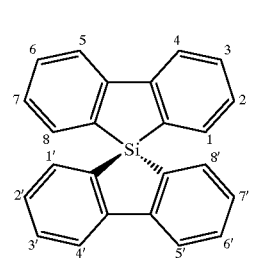

(V)

Compounds of the formula (IIIa) can be prepared, for example, starting from a tetrahalogenation in the 2,2',7,7' positions of 9,9'-spirobi-9-silafluorene and a subsequent substitution reaction, which are known from analogous C-spiro compounds (see, for example, U.S. Pat. No. 5,026, 894). This can lead, for example, by the corresponding cyano compounds, to aldehyde or carboxylic acid functionality which, can be used, for example, for constructing heterocycles.

Compounds of the formula (IIIb) can be prepared, for example, by a method similar to that for formula (IIIa), the stoichiometric ratios in the reaction being chosen such that the 2,2' and 7,7' positions are functionalized (see, for example, J. H. Weisburger, E. K. Weisburger, F. E. Ray, J. Am. Chem. Soc. 1959, 72, 4253; F. K. Sutcliffe, H. M. Shahidi, D. Paterson, J. Soc. Dyers Colour 1978, 94, 306 and G. Haas, V. Prelog, Helv. Chim. Acta 1969, 52, 1202).

The compounds of the formula (IIIc) and (IIId) can be prepared, for example, via a dibromination in the 7,7'-position of the 2,2'-dicyano-9,9'-spirobi-9-silafluorene, synthesized by a method similar to (IIIa), and subsequent reactions using a method similar to that for compounds (IIIa).

Compounds of the formula (IIIe)–(IIIg) can be prepared, for example, by choosing suitably substituted starting compounds for constructing the spirosilabifluorene, for example:

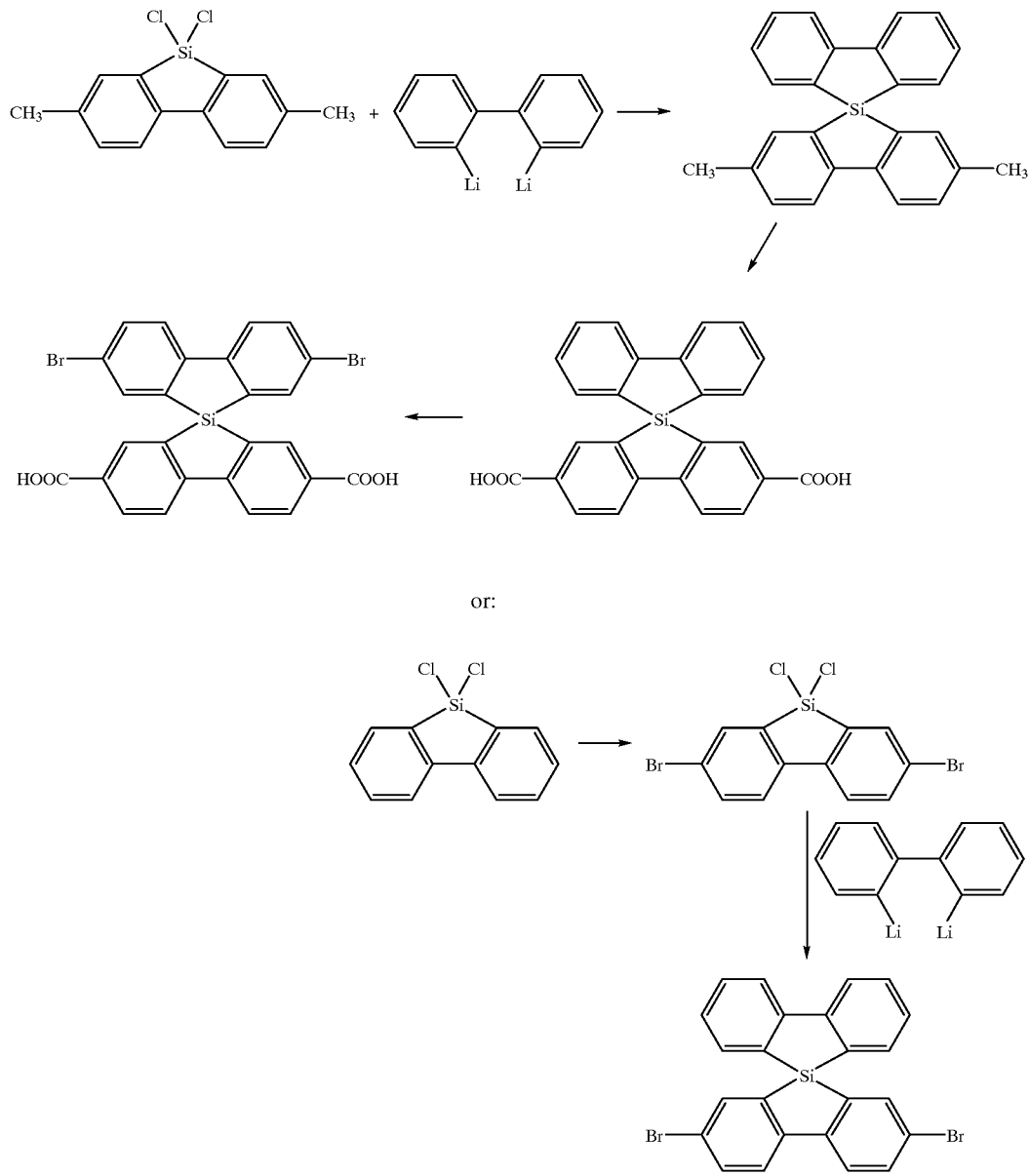

or:

It is also possible to use the synthesis sequences known to the person skilled in the art, for example nitration, reduction, diazotization and the Sandmeyer reaction. For the synthesis of the K, L, M, N groups, reference may be made, for example, to DE-A 23 44 732, 24 50 088, 24 29 093, 25 02 904, 26 36 684, 27 01 591 and 27 52 975 for compounds containing 1,4-phenylene groups; DE-A 26 41 724 for compounds containing pyrimidin-2,5-diyl groups; DE-A 40 26 223 and EP-A 03 91 203 for compounds containing pyridin-2,5-diyl groups; DE-A 32 31 462 for compounds containing pyridazin-3,6-diyl groups; N. Miyaura, T. Yanagi and A. Suzuki in Synthetic Communications 11 (1981) 513 to 519, DE-A-3 930 663, M. J. Sharp, W. Cheng, V. Snieckus in Tetrahedron Letters 28 (1987), 5093; G. W. Gray in J. Chem. Soc. Perkin Trans 11 (1989) 2041 and Mol. Cryst. Liq. Cryst. 172 (1989) 165, Mol. Cryst. Liq. Cryst. 204 (1991) 43 and 91; EP-A 0 449 015; WO 89/12039; WO 89/03821; EP-A 0 354 434 for the direct linking of aromatics and heteroaromatics.

The preparation of disubstituted pyridines, disubstituted pyrazines, disubstituted pyrimidines and disubstituted pyridazines is given, for example, in the appropriate volumes of the series "The Chemistry of Heterocyclic Compounds" by A. Weissberger and E. C. Taylor (editors).

The spiro compounds described above exhibit an unusually marked fluorescence in the dissolved, finely distributed or solid state. They are used for the optical brightening of many different synthetic, semisynthetic or natural organic materials or substances which contain organic materials.

The invention thus further provides for the use of spiro compounds of the formulae (I) to (V) as optical brighteners.

The invention further provides a method of optical brightening which comprises adding to the material to be optically brightened one or more spiro compounds of the formulae (I) to (V).

Examples of groups of materials which are suitable for optical brightening are the following:

I. Synthetic, high-molecular-weight materials:

a) Polymerization products based on compounds containing at least one polymerizable carbon-carbon double bond, i.e. their homo- or copolymers and their post-treatment products, such as, for example, crosslinking, graft or degradation products, polymer sections or products obtained by modifying reactive groups, for example polymers based on unsaturated carboxylic acids or their derivatives, in particular acrylic compounds (such as acrylates, acrylic acid, acrylonitrile, acrylamides and their derivatives or their methacrylic analogs), polymers of olefins (such as, for example, ethylene, propylene, styrenes or dienes, and also ABS polymers), polymers based on vinyl and vinylidene compounds (such as vinyl chloride and vinyl alkcohol), b) Polymerization products obtainable by ring opening, e.g. polyamides of the polycaprolactam type, and also polymers obtainable either by polyaddition or by polycondensation, such as polyethers or polyacetals, c) Polycondensation products or precondensates based on bi- or polyfunctional compounds containing condensable groups, their homo- and co-condensation products, and products of post-treatment, such as, for example, polyesters, in particular saturated (e.g. ethylene glycol terephthalic acid polyesters) or unsaturated (e.g. maleic acid dialcohol polycondensates and their crosslinking products with copolymerizable vinyl monomers), unbranched (including those based on polyhydric alcohols, such as alkyd resins) polyesters, polyamides (e.g. hexamethylenediamine adipate), maleic resins, melamine resins, their precondensates and analogs, polycarbonates, silicones, d) Polyaddition products, such as polyurethanes (crosslinked and noncrosslinked) and epoxy resins.

II. Semisynthetic materials, e.g. cellulose esters having varying degrees of esterification (e.g. so-called 2½ acetate, triacetate) or cellulose ethers, regenerated cellulose (viscose, cuprammonia cellulose) or their post-treatment products, or casein polymers.

III. Natural organic materials of an animal or vegetable origin, for example those based on cellulose or proteins, such as cotton, wool, linen, silk, natural "coating resins", starch, casein.

Preferred organic materials are those based on polyester, polyethylene, polypropylene, polystyrene, acrylic polymers, polyamide, polymethane, polyvinyl chloride, acetylcellulose, polyethylene terephthalate and engineering plastics, such as, for example, aramid fibers.

The organic materials which are to be optically brightened can belong to very many different types of processing states (raw materials, semifinished products or finished products). On the one hand, they can be in the form of very many differently shaped structures, for example as predominantly three-dimensional articles, such as plates, profiles, injection moldings, various workpieces, chips, granules or foam materials, and also as predominantly two-dimensional articles, such as films, foils, surface coatings, impregnations and coverings, or as predominantly one-dimensional articles, such as threads, fibers, flocks and wires. On the other hand, these materials can also be in an unshaped state in very many different homogeneous or nonhomogeneous distribution forms, e.g. as powders, solutions, emulsions, dispersions, lattices, pastes or waxes.

The compounds which are to be used according to the invention are especially important as optical brighteners for polymers, in particular transparent polymers.

Fiber materials can, for example, be in the form of continuous threads (drawn or undrawn), staple fibers, flocs, strands, textile threads, yams, twisted yams, nonwovens, felts, waddings, floc structures or as textile fabrics or textile composites, knitted fabrics and also papers, cards or pulps.

Where fibers, which can be in the form of staple fibers or continuous fibers, in the form of threads, wovens, knits, nonwovens, flocked substrates or composites, are to be optically brightened according to the invention, this is advantageously carried out in an aqueous medium, in which the compounds in question are present in finely dispersed form (suspensions, microdispersions, in some instances solutions). Where appropriate, dispersants, stabilizers, wetting agents and other auxiliaries can be added during the treatment.

Depending on the brightener compound type used, it may prove to be advantageous to work in a neutral or alkaline or acidic liquor. The treatment is usually carried out at temperatures of from 20° C. to 140° C., for example at or around the boiling temperature of the liquor. Because of the outstanding temperature stability of the spiro compounds, it is also possible to choose liquor temperatures up to 400° C. For the finishing of textile substrates according to the invention, solutions or emulsions in organic solvents are also suitable, as is the practice in dyeing in so-called solvent dyeing (pad mangle heat setting application, exhaust dyeing method in dyeing machines).

According to the invention, the optical brighteners can, for example, also be used for brightening pulps, also in the presence of, for example, cationic retaining agents and other additives.

The spiro compounds can also be added to or incorporated into the materials before or during shaping. Thus, it is, for example, possible to add them during the preparation of films, foils (e.g. rolling-in in polyvinyl chloride at elevated temperature) or of molded articles of a compression molding material or injection molding composition. A particular advantage of the spiro compounds is that even higher processing temperatures (up to 400° C.) than those customarily used hitherto can be used. In particular, this has opened up the possibility of brightening engineering plastics which require higher processing temperatures (e.g. aramid fibers).

Where the materials are shaped using spinning methods or by spinning dopes, the optical brighteners can be applied by the following methods:

addition to the starting substances (e.g. monomers) or intermediates (e.g. precondensates, prepolymers), i.e. before or during polymerization, polycondensation or polyaddition, dusting on to polymerization chips or granules for spinning dopes, liquor dyeing of polymerization chips or granules for spinning dopes, metered addition to spinning melts or spinning solutions. As a result of the absolute stability to sodium rhodanide, the incorporation into spinning dopes for the preparation of polyacrylonitrile fibers in the wet spinning process based on rhodanide-containing spinning and precipitation baths is of particular interest application to tows prior to drawing.

According to the present invention, the optical brighteners can, for example, be used in the following types of application:

a) mixtures or molecular dispersions containing polymers, preferably transparent polymers, such as acrylates, methacrylates, carbonates, polyesters (e.g. PET), polyethers or epoxy resins, b) mixtures containing dyes (nuancing) or pigments (colored or, in particular, also white pigments) or as an additive to dyeing baths, printing, discharge or reserve pastes, and also for the post-treatment of dyeings, prints or discharges, c) in mixtures with carriers, wetting agents, plasticizers, swelling agents, antioxidants, antifungicides and antibactericides, light protection agents, heat stabilizers, chemical bleaches (for example chlorite bleaches, hydrogen peroxide or peroxidic bleaches, percarboxylic acid bleaches, bleaching bath additives); the addition of reducing compounds, for example, sulfur compounds, is important in the case of types of spirobifluorene compounds. Particularly preferred commercial forms are concentrated, aqueous solutions. The sulfur compounds which have a reducing action can either be organic or inorganic in nature and are preferably water-soluble. Suitable examples are dithionites, pyrosulfites, sulfites, sulfides, thiosulfates and thiocyanates (e.g. potassium rhodanide) in the form of their salts (e.g. alkali metal, alkaline earth metal or ammonium salts) as aqueous solutions, in solid form or, as far as is known, also in the form of the free acids or their anhydrides, such as sulfur dioxide. Examples of organic compounds are mercaptans, such as thioglycolic acid, mercaptoethanol, 4-hydroxy-2-mercapto-3,3'-dithiodipropionic acid, sulfinates, such as sodium formaldehyde sulfoxylate or formamidinesulfinic acid and thiourea. Particular preference is given to sodium dithionite.

The amount of sulfur compound is generally 0.05–10 mol %, based on the brightener, preferably 0.5–5 mol %, d) in a mixture with crosslinkers, finishing agents (e.g. starch or synthetic finishing agents) and in combination with many different textile finishing procedures, in particular synthetic-resin finishes (e.g. creaseproof finishes, such as "wash-and-wear", "permanent-press", "no-iron"), and also antistatic finishes or antimicrobial finishes, e) incorporation of the optical brighteners into polymeric carrier materials (polymerization, polycondensation or polyaddition products) in dissolved or dispersed form for applications in coating, impregnation or binding materials (solutions, dispersions, emulsions) for textiles, nonwovens, paper, leather, f) as additives for "masterbatches", g) as additives for many different types of industrial products in order to make them more salable (e.g. to improve the appearance of soaps, detergents, pigments, PET bottles, aramid fibers and sewing threads for sport articles, shoes, tear-resistant ropes, bulletproof vests, roofing felt, disposable films), h) in combination with other substances which have an optically brightening effect, in particular mixtures of optical brighteners consisting of from 1 to 60% by weight of a brightener from the series of bisbenzoxazolyl-substituted spirobifluorenes and from 99 to 40% by weight of one or more standard commercial brighteners, such as, for example, brighteners from the series of coumarin, stilbene or pyrene brighteners. Since some of the Spiro compounds produce brightening effects with a green shade, it is particularly advantageous to use them together with brighteners which produce reddish brightening effects (e.g. compounds from the class of 2-stilbenylnaphthotriazoles). Preference is also given to mixtures of spiro compounds, the optimum mixing ratio depending in each case on the type of spiro compounds in question and being readily determinable by simple preliminary experiments.

In some cases, such mixtures can also result in unexpected synergistic effects with respect to the brightness and the brilliance of the brightenings, i) in spinning bath preparations, i.e. as additives for spinning baths as are used for improving slip for the further processing of synthetic fibers, or from a specific liquor prior to drawing the fibers, j) as scintillators for various purposes of a photographic nature, e.g. for electrophotographic reproductions or supersensitization, for the optical brightening of photographic layers.

For various reasons, it is often expedient to use the brightener not as it is, i.e. pure, but mixed with a variety of auxiliaries and subduing agents, such as anhydrous sodium sulfate, sodium sulfate decahydrate, sodium chloride, sodium carbonate, alkali metal phosphates, such as sodium or potassium tripolyphosphates or alkali metal silicates.

In certain cases, the brighteners are fully activated by means of a post-treatment. This can, for example, be a chemical treatment (e.g. acid treatment), a thermal treatment (e.g. heat) or a combined chemical/thermal treatment. An expedient way of carrying out the optical brightening of a series of fiber substances, e.g. of polyester fibers, using the brighteners thus involves impregnating these fibers with aqueous dispersions (where appropriate also solutions) of the brightener at temperatures between 80° C. and room temperature and subjecting them to a dry heat treatment at temperatures above 100° C., it generally being advisable to dry the fiber material beforehand at moderately elevated temperature, e.g. at at least 60° C. to about 180° C. The heat treatment in the dry state is then advantageously carried out at temperatures between 120 and 225° C., for example by warming in a drying chamber, by ironing in the given temperature range or by treating with dry, superheated steam. The drying and dry heat treatment can also be carried out directly after one another or be carried out together in a single operation.

The amount of optical brightener to be used according to the invention, based on the material to be brightened, can vary within wide limits. Even using extremely small amounts, in certain cases e.g. amounts of $10^{-6}$ percent by weight, it is possible to achieve a clear and lasting effect. It is, however, also possible to use amounts up to about 3% by weight in some instances. For many practical requirements, amounts between 0.00001 and 0.5 percent by weight are preferably of interest. For some applications, for example as transformation material, in particular in layered form, for UV light for increasing the efficiency in solar cells, the amount of the novel brightener can also be significantly higher (from 3 to 90% by weight, preferably from 10 to 75% by weight, particularly preferably from 10 to 50% by weight). The component(s) additionally used, preferably transparent polymers, in these cases usually adopt(s) the role of a binder.

In this connection, it is particularly advantageous that at least the spiro compounds of the formula (I) can be mixed in any ratio with known polymers.

The spiro compounds are also suitable as additives for wash baths or for industrial and domestic detergents, in particular also for concentrated, liquid or solid detergents. For wash baths, the brighteners are expediently added in the form of their solutions in water or organic solvents or else in fine distribution as aqueous dispersions. For domestic or industrial detergents, they are advantageously used in any phase of the preparation process of the detergent, e.g. the "slurry", prior to atomization. They can be added either in the form of a solution or dispersion in water or other solvents or else without auxiliaries as a dry brightener powder. It is possible, for example, to mix, knead or grind the brightener with the detersive substances, and add it in this form to the finished detergent powder. They can, however, also be sprayed onto the finished detergent in dissolved or predispersed form.

Suitable detergents are the known mixtures of detersive substances, such as, for example, soaps in the form of chips and powders, synthetics, soluble salts of sulfonic half-esters of higher fatty alcohols, higher and/or alkyl-polysubstituted arylsulfonic acids, sulfocarboxylates of medium to higher alcohols, fatty acid acylaminoalkyl- or -aminoaryl glycerol sulfonates, phosphonates of fatty alcohols etc., and also customary surfactants, for example the water-soluble products obtained from the addition of an, alkylene oxide or an equivalent compound with a reactive hydrogen atom of a hydrophobic compound. The hydrophobic organic products can be heterocycles and particularly aliphatics or aromatics. Preference is given to higher aliphatic alcohols and alkylphenols, although others, e.g. carboxylic acids, carboxamides, mercaptans and sulfamides, can also be used. Preferred nonionogenic compounds are the addition products of ethylene oxide with higher aliphatic alcohols having from 6 to 50 and above carbon atoms. The amount of ethylene oxide can vary within wide limits, but at least 5 mol of ethylene oxide are generally consumed per mole of hydrophobic substance. Instead of some or all of the ethylene oxide, it is possible to use other lower alkylene oxides, for example propylene oxide and butylene oxide.

Examples of other suitable nonionogenic surfactants are:

a) polyoxyalkylene esters of organic acids, such as higher fatty acids, resin acids, tallow oil acids and acids of the oxidation products of petroleum, the esters of which usually have from 10 to 22 carbon atoms in the acid moiety and contain from about 12 to about 30 moles of ethylene oxide or its equivalent.

b) alkylene oxide adducts of higher fatty acid amides, the fatty acid moiety generally having from 8 to 22 carbon atoms and being condensed with from 10 to 50 mol of ethylene oxide. The corresponding carboxamides and sulfamides can likewise be used.

In the preparation of concentrated detergents, the nonionogenic surfactants used are preferably oxalkylated higher aliphatic alcohols, the fatty alcohols having at least 6, and preferably at least 8, carbon atoms. Preferred alcohols are lauryl, myristyl, cetyl, stearyl and oleyl alcohol, which are condensed with at least 6 mol of ethylene oxide. A typical nonionogenic product is the addition product of an aliphatic alcohol having 12–13 carbon atoms with about 6.5 mol of ethylene oxide. The corresponding alkylmercaptans can, following condensation with ethylene oxide, likewise be used as nonionogenic surfactants.

The alkoxylated higher alcohols are particularly suitable for domestic detergents since they are readily biodegradable and are readily compatible with cationic surfactants and textile softeners and customary additives.

Examples of suitable builders are alkali metal poly- and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborate, nitrilotriacetic acid, ethylenediaminotetraacetic acid, foam stabilizers, such as alkanolamides of higher fatty acids. The detergents may additionally comprise, for example: antistatics, refatting skin protectants, such as lanolin, enzymes, antimicrobial substances, perfumes, dyes and cationic textile softeners.

Suitable cationic textile softeners are especially quaternary derivatives of ammonia and/or of imidazoline having 2 long-chain, aliphatic saturated or unsaturated radicals.

Examples of quaternary ammonium softeners are: tallyltrimethylammonium chloride, ditallyldimethylammonium chloride; ditallyldimethylammonium sulfate, dihexadecyldimethylammonium chloride; dioctadecyldimethylammonium chloride, dieicosyldimethylammonium chloride, didocosyldimethylammonium chloride, dihexadecyidiethylammonium chloride, dihexadecylmethylammonium acetate, ditallyldipropylammonium phosphate, ditallyldimethylammonium nitrate, dicocoyldimethammonium chloride, 1-methyl-1-stearylamidoethyl-2-heptadecylimidazolinium methosulfate, 1-methyl-1-palmitoylamidoethyl-2-octadecylimidazolinium chloride, 2-tallyl-1-methyl-1-talloylamidoethylimidazolinium methosulfate.

Further examples of suitable textile softeners are: 1-methyl-1-oleylamidoethyl-2-octadecylimidazolinium chloride, 1-methyl-1-talloylamidoethyl-2-tallylimidazolinium chloride, ditallyldimethylammonium chloride, 1-methyl-1-oleylamidoethyl-2-oleylimidazolinium methosulfate, 1-methyl-1-talloylamidoethyl-2-tallylimidazolinium methosulfate.

The spiro compounds have the particular advantage that they are also effective in the presence of active-chlorine donors, such as hypochlorite, and can be used without considerable losses in the effects in wash baths containing nonionogenic detergents, e.g. alkylphenol polyglycol ethers.

The spiro compounds are added in amounts of 0.00001–1% or above, based on the weight of the liquid or pulverulent, finished detergent. Wash liquors which contain the given amounts of claimed optical brighteners impart a brilliant appearance in daylight in the washing of textiles made from cellulose fibers, polyamide fibers, resin-finished cellulose fibers, polyester fibers, wool etc.

The washing treatment is, for example carried out as follows:

Said textiles are treated for from 1 to 30 minutes at from 20 to 100° C. in a washing bath which comprises from 1 to 10 g/kg of a compound detergent containing a builder and from 0.0005 to 1%, based on the detergent weight, of the claimed brightener. The liquor ratio can be from 3:1 to 50:1. After washing, rinsing and drying is carried out as usual. The wash bath can contain, as bleach additive, 0.2 g/l of active chlorine (e.g. hypochlorite) or from 0.1 to 2 g/l of sodium perborate.

The spiro compounds can also be used in the after-rinse bath, as is customary for merely imparting softness, antistatic properties, antisoil effects, perfume notes etc. In particular, they are suitable for use in laundry post-treatment compositions which contain cationic softeners.

EXAMPLES

A. Starting compounds a) Synthesis of 9,9'-spirobifluorene 6.3 g of magnesium turnings and 50 mg of anthracene were introduced under argon into 120 ml of dry diethyl ether in a 1 I three-neck flask fitted with a reflux condenser, and the magnesium was activated for 15 min using ultrasound. 62 g of 2-bromobiphenyl were dissolved in 60 ml of dry diethyl ether. Approximately 10 ml of this solution were added to the initial charge of magnesium in order to start the Grignard reaction.

After the reaction had started, the 2-bromobiphenyl solution was added dropwise with further ultrasound treatment at a rate such that the solution was gently refluxed. When addition was complete, the reaction mixture was refluxed with ultrasound for a further hour.

48.8 g of 9-fluorenone were dissolved in 400 ml of dry diethyl ether and added dropwise with further ultrasound treatment to the Grignard solution. When addition was complete, the mixture was boiled for a further 2 h. The yellow magnesium complex of 9-(2-biphenyl)-9-fluorenol which precipitated out when the reaction mixture was cooled was filtered off with suction and washed with a small amount of ether. The magnesium complex was hydrolyzed in 800 ml of iced water which contained 40 g of ammonium chloride. After the mixture had been stirred for 60 min, the 9-(2-biphenyl)-9-fluorenol formed was filtered off with suction, washed with water and sucked dry.

The dried 9-(2-biphenyl)-9-fluorenol was then dissolved in 500 ml of glacial acetic acid at elevated temperature. 0.5 ml of conc. hydrochloric acid was added to this solution. The solution was allowed to boil for a few minutes, and the 9,9'-spirobifluorene which formed was precipitated out of the hot solution with water (addition of water until the onset of turbidity). After cooling, the product was filtered off with suction and washed with water. The dried product was recrystallized from ethanol in order to purify it further. This gave 66 g (80%, based on 2-bromobiphenyl) of 9,9'-spirobifluorene as colorless crystals, m.p. 198° C.

b) 2,2'-Dibromo-9,9'-spirobifluorene (F. K. Sutcliffe, H. M. Shahidi, D. Patterson, J. Soc. Dyers Colour 94 (1978) 306)

3.26 g (10.3 mmol) of 9,9'-spirobifluorene were dissolved in 30 ml of methylene chloride, and 5 mg of $FeCl_3$ (anhydrous) were added thereto as catalyst. The reaction flask was protected from the entry of light. 1.12 ml (21.8 mmol) of bromine in 5 ml of methylene chloride were added dropwise with stirring over the course of 30 min. After 24 h, the resulting brown solution was washed with saturated, aqueous $NaHCO_3$ solution and water in order to remove excess bromine. After drying over $Na_2SO_4$, the organic phase was concentrated by. evaporation on a rotary evaporator. The white residue was recrystallized from methanol to give 3.45 g (70%) of the dibromo compound as colorless crystals, m.p. 240° C.

c) 2,2',7,7'-Tetrabromo-9,9'-spirobifluorene 80 mg (0.5 mmol) of anhydrous $FeCl_3$ were added to a solution of 3.16 g (10.0 mmol) of 9,9'-spirobifluorene in 30 ml of methylene chloride, and 2.1 ml (41 mmol) of bromine in 5 ml of methylene chloride were added dropwise over 10 min. The solution was refluxed for 6 h. Upon cooling, the product precipitated out. The precipitate was filtered off with suction and washed with a small amount of cold methylene chloride. Drying gave 6.0 g (95%) of the tetrabromo compound as a white solid.

d) 2-Bromo-9,9'-spirobifluorene and 2,2',7-tribromo-9,9'-spirobifluorene were prepared in an analogous manner with modified stoichiometry.

e) 9,9'-Spirobifluorene-2,2'-dicarboxylic acid from 2,2'-dibromo-9,9'-spirobifluorene via 2,2'-dicyano-9,9'-spirobifluorene 1.19 g of 2,2'-dibromo-9,9'-spirobifluorene and 0.54 g of CuCN were refluxed in 5 ml of DMF for 6 h. The resulting brown mixture was poured into a mixture of 3 g of $FeCl_3$ (hydrat.) and 1.5 ml of conc. hydrochloric acid in 20 ml of water. The mixture was held at from 60 to 70° C. for 30 min in order to destroy the Cu complex. The hot aqueous solution was extracted twice with toluene. The organic phases were then washed with dilute hydrochloric acid, water and 10% strength aqeuous NaOH. The organic phase was filtered and concentrated by evaporation. The resulting yellow residue was recrystallized from methanol. This gave 0.72 g (80%) of 2,2'-dicyano-9,9'-spirobifluorene as pale yellowish crystals (melting range 215 to 245° C.).

3 g of 2,2'-dicyano-9,9'-spirobifluorene were refluxed with 25 ml of 30% strength aqueous NaOH and 30 ml of ethanol for 6 h. The disodium salt of spirobifluorenedicarboxylic acid precipitated out as a yellow preipitate, which was filtered off and heated in 25% strength aqueous HCl in order to obtain the free acid. The spirobifluoremedicarboxylic acid was recrystallized from glacial acetic acid. This gave 2.2 g (66.6%) of white crystals (m.p. 376° C., IR band 1685 $cm^{-1}$ C=O).

9,9'-Spirobifluorene-2,2',7,7'-tetracarboxylic acid was prepared from 2,2',7,7'-tetrabromo-9,9'-spirobifluorene in an analogous manner.

f) 9,9-Spirobifluorene-2,2 '-dicarboxylic acid from 9,9'-spirofluorene via 2,2'-diacetyl-9,9'-spirobifluorene (G. Haas, V. Prelog, Helv. Chim. Acta 52 (1969) 1202; V. Prelog, D. Bedekovic, Helv. Chim. Acta 62 (1979) 2285)

9.0 g of finely powdered, anhydrous $AlCl_3$ were added to a solution of 3.17 g of 9,9'-spirobifluorene in 30 ml of abs. carbon disulfide, and then 1.58 g of acetyl chloride in 5 ml of abs. carbon disulfide were added dropwise over the course of 10 min with stirring, and the mixture was then refluxed for 1 hour. 100 g of ice and 50 ml of 2n hydrochloric acid were added at 0° C. to the mixture which had been evaporated to dryness under reduced pressure. After customary work-up, the crude product was separated by chromatography using benzene/ethyl acetate (10:1) on silica gel. This gave 3.62 g (89%) of 2,2'-diacetyl-9,9'-spirobifluorene (recrystallized from chloroform/ethyl acetate, m.p. 255 to 257° C.) and 204 mg of 2-acetyl-9,9'-spirobifluorene (recrystallized from chloroforan/benzene, m.p. 225° C.). [in addition, in the chromatography, 2,2',7-triacetyl-9,9'-spirobifluorene (m.p. 258 to 260° C.) and 2,2',7,7'-tetraacetyl- 9,9'-spirobifluorene (m.p. >300° C.) were also isolated, recrystallized from ethyl acetate/hexane].

2,2',7-Triacetyl- and 2,2',7,7'-tetraacetyl-9,9'-spirobifluorene were obtained with modified stoichiometry as the main product.

At 0° C., first 7.2 g of bromine and then a solution of 3.0 g of 2,2'-diacetyl-9,9'-spirobifluorene in a small amount of dioxane were added dropwise with stirring to a solution of 6.0 g of sodium hydroxide in 30 ml of water. After the mixture had been stirred for a further 1 hour at room temperature, 1 g of sodium hydrogensulfite, dissolved in 20 ml of water, was added to the clear yellow solution. Following acidification with conc. hydrochloric acid, the colorless product which had precipitated out was filtered off and washed with a small amount of water. Recrystallization from ethanol produced 9,9'-spirobifluorene-2,2'-dicarboxylic acid as water-clear prisms (m.p. 352° C.).

9,9'-Spirobifluorene-2-carboxylic acid, 9,9'-spirobifluorene-2,2',7-tricarboxylic acid and 9,9'-spirobifluorene-2,2',7,7'-tetracarboxylic acid were prepared in an analogous manner.

g) 2,2'-Bis(bromomethyl)-9,9'-spirobifluorene from 2,2'-dicarboxy-9,9'-spirobifluorene via 9,9'-spirobifluorene-2,2'-dimethanol (V. Prelog, D. Bedekovicc, Helv. Chim. Acta 62 (1979) 2285)

At room temperature, 10 g of a 70% by weight strength solution of sodium dihydro-bis(2-methoxyethoxy)aluminate (Fluka) in benzene were slowly added dropwise to a suspension of 2.0 g of 2,2'-dicarboxy-9,9'-spirobifluorene (free carboxylic acid) in 20 ml of benzene. After the mixture had been refluxed for 2 h, during which time the carboxylic acid dissolved, the excess reducing agent was decomposed at 10° C. using water, the mixture was acidified using conc. hydrochloric acid and extracted by shaking with chloroform.

The organic phase was washed with water, dried over magnesium sulfate and evaporated, and the residue was recrystallized from benzene. This gave 1.57 g of 9,9'-spirobifluorene-2,2'-dimethanol (m.p. 254 to 255° C.). 91.5 g of 33% strength aqueous solution of hydrogen bromide in glacial acetic acid were added dropwise to a solution of 13.5 g of 9,9'-spirofluorene-2,2'-dimethanol in 400 ml of benzene, and the mixture was refluxed for 7 h. 200 ml of water were then added, and the organic phase was washed with water, dried with magnesium sulfate and evaporated. Chromatography on silica gel using benzene produced 11.7 g of 2,2'-bis(bromomethyl)-9,9'-spirobifluorene as colorless flakes (m.p. 175 to 177° C.).

h) 5 g of chromium(VI) oxide on graphite (Seloxcette, Alpha Inorganics) were added to a solution of 380 mg of 9,9'-spirobifluorene-2,2'-dimethanol in 15 ml of toluene, and the mixture was refluxed under nitrogen for 48 h. The mixture was then filtered with suction using a glass suction filter, and the filtrate was evaporated. Chromatography on silica gel using chloroform and crystallization from methylene chloride/ether produced 152 mg of 9,9'-spirobifluorene-2,2'-dicarbaldehyde (m.p. >300° C.) and 204 mg of 2'-hydroxymethyl-9,9'-spirobifluorene-2-carbaldehyde (m.p. 262 to 263° C.).

i) 2,2'-Diamino-9,9'-spirobifluorene

A mixture of 150 ml of conc. aqueous $HNO_3$ and 150 ml of glacial acetic acid were added dropwise to a boiling solution of 15.1 g of 9,9'-spirobifluorene in 500 ml of glacial acetic acid over a period of 30 min, and then the solution was refluxed for a further 75 min. After the solution had cooled and been allowed to stand for 1 hour, the same volume of water was added, resulting in precipitation of the product. Filtration with suction gave 18.5 g of yellow crystals (m.p. 220 to 224° C.) of 2,2'-dinitro-9,9'-spirobifluorene. Recrystallization from 250 ml of glacial acetic acid gave 12.7 g of pale yellow crystal needles (m.p. 245 to 249° C., analytically pure 249 to 250° C.).

A mixture of 4.0 ml of dinitrospirobifluorene and 4.0 g of iron powder were refluxed in 100 ml of ethanol, while 15 ml of conc. HCl were added dropwise over a period of 30 min. After the mixture had been refluxed for a further 30 min, excess iron was filtered off. The green filtrate was introduced into a solution of 400 ml of water, 15 ml of conc. $NH_4OH$ and 20 g of Na,K tartrate. The white diamine was filtered off from the dark green solution of the iron complex. The diamine was purified by dissolving it in dilute HCl and, at room temperature, stirring it with activated carbon (Darco) and filtering. The filtered solution was neutralized with $NH_4OH$ dropwise with stirring (precision-ground glass stirrer), and the product which precipitated out was filtered off with suction. This gave 3.5 g of white 2,2'-diamino-9,9'-spirobifluorene, which was recrystallized from ethanol (m.p. 243° C.).

j) Synthesis of 2,2',7,7'-tetrabromo-9,9'-spirobifluorene by bromination of solid 9,9'-spirobifluorene using bromine vapor.

3.16 g (10 mmol) of finely powdered 9,9'-spirobifluorene were introduced into a flat porcelain evaporating dish (φ about 15 cm). This dish was placed in a desiccator (φ about 30 cm) on the perforated false bottom. 15.6 g (4.8 ml, 96 mmol) of bromine in a crystallizing dish were placed on the floor of the desiccator. The desiccator was sealed, although the aeration cock was opened so that the HBr which formed was able to escape. The desiccator was placed overnight in a fume cupboard. On the next day, the porcelain dish containing the product, which had been turned orange in color by the bromine, was removed from the desiccator and left to stand in the fume cupboard for at least a further 4 h so that excess bromine and HBr could escape.

The product was dissolved in 150 ml of dichloromethane and washed with, in each case, 50 ml of sodium sulfite solution (saturated), sodium hydrogencarbonate solution (saturated) and water until colorless. The dichloromethane solution was dried over sodium sulfate and concentrated by evaporation on the rotary evaporator. The product was purified by recrystallizing it from a 4:1 dichloromethane/pentane mixture. Yield 5.7 g (92%) of colorless crystals.

$^1$H-NMR (CDCl$_3$, ppm): 6.83 (d, J=1.83 Hz, 4H, H-1,1', 8,8'); 7.54 (dd, J=7.93,1.83 Hz, 4H, H-3,3',6,6'); 7.68 (d, J=7.93 Hz, 4H, H-4,4',5,5').

k) Synthesis of 2,2',4,4',7,7'-hexabromo-9,9'-spirobifluorene 200 mg of anhydrous FeCl$_3$ were added to a solution of 3.16 g (10 mmol) of 9,9'-spirobifluorene in 20 ml of methylene chloride, and the mixture was treated with ultrasound. The reaction flask was protected against the entry of light using Al foil. 9.85 g (3.15 ml, 62 mmol) of bromine in 5 ml of methylene chloride were then added dropwise at the boil over the course of 15 min. The solution was refluxed for a further 20 h and treated with ultrasound. After cooling, petroleum ether is added and the mixture is filtered with suction. The product is further purified by recrystallizing it from THF/methanol, and drying it for 5 h at 80° C.

Yield 6.15 g (77%) of colorless crystals.

$^1$H-NMR (CDCl$_3$, ppm): 6.76 (d, J=1.53 Hz, 2H, H-1,1); 6.84 (d, J=1.83 Hz, 2H, H-8,8); 7.60 (dd, J=8.54,1.83 Hz, 2H, H-6,6'); 7.75 (d, J=1.53 Hz, 2H, H-3,3'); 8.49 (d, J=8.54Hz, 2H, H-5,5').

l) Synthesis of 2,7-dibromo-9,9'-spirobifluorene

A Grignard reagent prepared from 0.72 g (30 mmol) of magnesium turnings and 5.1 ml (30 mmol) of 2-bromobiphenyl in 15 ml of diethyl ether was added dropwise to a boiling suspension of 10.0 g (29.6 mmol) of 2,7-dibromo-9-fluorenone in 100 ml of dry diethyl ether with stirring (in an ultrasound bath) over the course of 2 h. When addition is complete, the mixture is boiled for a further 3 hours. After cooling overnight, the precipitate which had formed was filtered off with suction and washed with cold ether. The magnesium complex which had been filtered off with suction was hydrolyzed in a solution of 15 g of ammonium chloride in 250 ml of iced water. After 1 h, the 9-(2-biphenylyl)-2,7-dibromo-9-fluorenol which formed was filtered off with suction, washed with water and was sucked dry. For the ring-closure reaction, the dried fluorenol was boiled for 6 hours in 100 ml of glacial acetic acid, after the additon of 3 drops of conc. HCl. The mixture was left to crystallize overnight, and the product which formed was filtered off with suction and washed with glacial acetic acid and water.

Yield: 11 g (77%) of 2,7-dibromo-9,9'-spirobifluorene. The product was further purified by recrystallizing it from THF.

$^1$H-NMR (CDCl$_3$, ppm): 6.73 (d, J=7.63 Hz, 2H, H-1',8'); 6.84 (d, J=1.83 Hz, 2H, H-1,8); 7.15 (td, J=7.63, 1.22Hz., 2H, H-2',7'); 7.41 (td, J=7.63, 1.22 Hz, 2H, H-3',6'); 7.48 (dd, J=8.24,1.83 Hz, 2H, H-3,6); 7.67 (d, J=8.24; 2H; H-4,5); 7.85 (d, J=7.63, 2H, H-4',5').

m) Synthesis of 2,7-dicarbethoxy-9,9'-spirobifluorene

A Grignard reagent prepared from 0.97 g (40 mmol) of magnesium turnings and 9.32 g (6.8 ml, 40 mmol) of 2-bromobiphenyl in 50 ml of dry diethyl ether was added dropwise to a boiling solution of 13 g (40 mmol) of 2,7-dicarbethoxy-9-fluorenone in 100 ml of dry diethyl ether over the course of 2 h. When addition was complete, the mixture was boiled for a further 3 hours. After cooling overnight, the precipitate formed was filtered off with suction and washed with cold ether. The magnesium complex was filtered off with suction and hydrolyzed in a solution of 15 g of ammonium chloride in 250 ml of iced water. After 1 h, the 9-(2-biphenylyl)-2,7-dicarbethoxy-9-fluorenol which had formed was filtered off with suction, washed with water and sucked dry. For the ring-closure reaction, the dried fluorenol was boiled for 6 hours in 100 ml of glacial acetic acid, following the addition of 3 drops of conc. HCl. The mixture was left to crystallize overnight, and the product which had formed was filtered off with suction and washed with glacial acetic acid and water.

Yield: 15.1 g (82%) of 2,7-dicarbethoxy-9,9'-spirobifluorene. The product was further purified by recrystallizing it from ethanol.

$^1$H-NMR (CDCl$_3$, ppm): 1.30 (t, J=7.12Hz, 6 H, ester-CH$_3$); 4.27 (q, J=7.12 Hz, 4H, ester-CH$_2$); 6.68 (d, J=7.63 Hz, 2H, H-1',8'); 7.11 (td, J=7.48, 1.22 Hz, 2H, H-2',7'); 7.40 (td, J=7.48, 1.22Hz, 4H, H-1, 8, 3',6'); 7.89 (dt, J=7.63, 0.92Hz, 2H, H-4',5'); 7.94 (dd, J=7.93, 0.6 Hz, 2H, H-4, 5); 8.12 (dd, J=7.93,1.53 Hz, 2H, H-3, 6).

n) Synthesis of 2,7-dibromo-2',7'-diiodo-9,9'-spirobifluorene

At 80° C., 5 ml of water were added to a suspension of 2.37 g of 2,7-dibromo-9,9'-spirobifluorene in 50 ml of glacial acetic acid in a 250 ml three-neck flask fitted with a reflux condenser and dropping funnel, and, after the addition of 2 ml of conc. sulfuric acid, 1.27 g of iodine, 0.53 g of iodic acid and 5 ml of carbon tetrachloride, the mixture was stirred until the color of the iodine disappeared. The mixture was then filtered with suction and washed well with water. After drying, the precipitate was dissolved in 150 ml of dichloromethane, and washed successively with Na$_2$SO$_3$ solution, NaHCO$_3$ solution and with water. The dichloromethane phase was dried over Na$_2$SO$_4$ and then evaporated. This gave colorless crystals of 2,7-dibromo-2',7'-diiodo-9,9'-spirobifluorene in quantitative yield. The product was further purified by recrystallizing it from dichloromethane/pentane.

$^1$H-NMR (CHCl$_3$, ppm): 6.80 (d, J=1.83 Hz, 2H), 6.99 (d, J=1.53 Hz, 2H), 7.51 (dd, J=8.24, 1.83 Hz, 2H), 7.54 (d, J=7.93 Hz, 2H), 7.65 (d, J=8.24Hz, 2H), 7.72 (dd, J=8.24, 1.53 Hz, 2H).

B. Synthesis examples

Example 1

2,2'-Bis(benzofuran-2-yl)-9,9'-spirobifluorene (by a method similar to W. Sahm, E. Schinzel, P. Jurges, Liebigs Ann.Chem. (1974) 523.)

2.7 g (22 mmol) of salicylaldehyde and 5.0 g (10 mmol) of 2,2'-bis(bromomethyl)-9,9'-spirobifluorene were dissolved in 15 ml of DMF at room temperature, and 0.9 g (22.5 mmol) of pulverized NaOH and a spatula tip of KI were added thereto. The mixture was heated to boiling and stirred for 1 h at the boiling temperature. After cooling, a mixture of 0.5 ml of conc. hydrochloric acid, 7 ml of water and 7 ml of methanol were added to the reaction solution. The stirring was continued at room temperature for a further 1 h, the crystalline reaction products were filtered off with suction, washed firstly with cold methanol, then with water and dried under reduced pressure at 60° C. This gave 4.6 g (79%) of the bisbenzyl phenyl ether.

2.1 g (22.5 mmol) of freshly distilled aniline were added to 5.85 g (10 mmol) of the bisbenzyl phenyl ether in 10 ml of toluene. A spatula tip of p-toluenesulfonic acid was added, and the mixture was heated to boiling at the water separator until water no longer separated off (about 3 to 5 h). As the reaction mixture cooled, the corresponding bisbenzylidenephenylamine crystallized out. The latter is filtered off with suction, washed with methanol and dried at 60° C. under reduced pressure. It was further purified by recrystallizing it from DMF.

7.35 g (10 mmol) of the bisbenzylidenephenylamine and 0.62 g (11 mmol) of KOH were introduced under nitrogen into 30 ml of DMF. The mixture is then heated with stirring at 100° C. for 4 h. After cooling to room temperature, the precipitate was filtered off with suction and washed with a small amount of DMF and water. After drying at 60° C. in a vacuum drying cabinet, the 2,2'-bis(benzofuran-2-yl)-9,9'-spirobifluorene was purified by recrystallization from methyl benzoate.

Example 2

2,2',7,7'-Tetra(benzofuran-2-yl)-9,9'-spirobifluorene was prepared with a correspondingly modified stoichiometry as in Example 1.

Example 3

2,2',7,7'-Tetraphenyl-9,9'-spirobifluorene 5 g (7.9 mmol) of 2,2',7,7'-tetrabromo-9,9'-spirobifluorene, 3.86 g (31.6 mmol) of phenylboronic acid, 331.5 mg (1.264 mmol) of triphenylphosphane and 70.9 mg (0.316 mmol) of palladium acetate were slurried in a mixture of 65 ml of toluene and 40 ml of aqueous sodium carbonate solution (2 M). The mixture was refluxed for 24 h with vigorous stirring. After cooling to room temperature, the mixture was filtered with suction, washed with water and dried at 50° C. under reduced pressure. This gave 2.58 g of product. The filtrate was extracted with 50 ml of toluene, and the dried organic phase was evaporated to dryness. This gave a further 1.67 g of product. Overall yield 4.25 g (86%)

Example 4

Synthesis of 2,2',7,7'-tetrakis(biphenyl-4-yl)-9,9'-spirobifluorene 5.5 g of tetrabromospirobifluorene, 7.2 g of biphenylboronic acid and 400 mg of tetrakis(triphenylphosphine) palladium were slurried in a mixture of 100 ml of toluene and 50 ml of potassium carbonate solution in a 250 ml two-neck flask fitted with a reflux condenser and precision-ground glass stirrer. The mixture was refluxed for 8 h with stirring using a precision-ground glass stirrer and with protective-gas blanketing. After cooling, the product was filtered off with suction, and the precipitate was washed with water and dried. In the filtrate, the toluene phase was separated off, and the aqueous phase was extracted by shaking once with chloroform. The combined organic phases were dried over sodium sulfate and concentrated by evaporation on a rotary evaporator; this gave a second fraction of the product. The two product fractions were combined (8 g) and dissolved in chloroform. The chloroform solution was boiled with activated carbon and filtered through a short column containing silica gel. Concentration by evaporation on a rotary evaporator and recrystallization from chloroform/pentane gave colorless crystals which had a blue fluorescence in UV light.

Melting point 408° C. (DSC).

$^1$H-NMR (CDCl$_3$, ppm): 7.14 (d, J=1.53 Hz, 4H); 7.75 (dd, J=7.93,1.53 Hz, 4H); 8.01 (d, J=7.93 Hz, 4H); 7.34 (dd, J=7.32, 1.37 Hz, 4H); 7.42 (t, J=7.32Hz, 8H); 7.58 (24H).

Example 5

Synthesis of 2,2',4,4',7,7'-hexakis(biphenyl-4-yl)-9,9'-spirobifluorene 1.6 g of hexabromospirofluorene and 3 g of biphenylboronic acid were slurried in a mixture of 50 ml of toluene and 50 ml of 1 M potassium carbonate solution in a 250 ml two-neck flask fitted with a reflux condenser and precision-ground glass stirrer. The mixture was refluxed under nitrogen, and 115 mg of tetrakis(triphenylphosphine) palladium in 5 ml of toluene were added. The mixture was refluxed with stirring for 7 h. When the reaction was complete, the cooled solution was filtered, and the filtrate was extracted by shaking twice with water (to achieve better phase separation, chloroform was added). The organic phase was dried over sodium sulfate, filtered through a short column containing silica gel and then concentrated by evaporation. It was further purified by recrystallizing it from dichloromethane/pentane. This gave 2 g (80%) of colorless crystals which have a blue fluorescence in UV light.

$^{13}$C-NMR [360 MHz.; ATP, broad-band decoupled] (CDCl$_3$, ppm): 65.94 (1C, spiro-C); 126.95 (6C, CH), 126.97 (6C, CH), 127.17 (6C, CH), 127.35 (6C, CH), 127.36 (6C, CH), 127.39 (6C, CH), 127.52 (6C, CH), 128.73 (6C, CH), 128.75 (6C, CH), 128.94 (6C, CH), 129.90 (4C, CH), 137.77 (2C), 137.86 (2C), 139.43 (2C), 139.69 (2C), 139.89 (2C), 140.09 (2C), 140.17 (2C), 140.22 (2C), 140.30 (2C), 140.63 (2C), 140.64 (2C), 140.68 (2C), 140.72 (2C), 140.74 (2C), 150.45 (2C), 150.92 (2C).

Example 6

Synthesis of 2,2'-bis[(5(p-t-butylphenyl)-1,3,4-oxadiazol-2yl]-9,9'-spirobifluorene from 9,9'-spirobifluorene-2,2'-dicarbonyl chloride and 5(4-t-butylphenyl)tetrazole a) Synthesis of 5(4-t-butylphenyl)tetrazole 4.99 of p-t-butylbenzonitrile, 3.82 g of lithium chloride and 5.85 g of sodium azide and 8.2 g of triethylammonium bromide in 100 ml of DMF were heated at 120° C. for 8 h in a 250 ml round-bottom flask fitted with a reflux condenser. After cooling to room temperature, 100 ml of water were added, and, in an ice bath, dilute hydrochloric acid was added until no more precipitate formed. The mixture was filtered with suction, and the precipitate was washed with water and dried. Recrystallization from ethanol/water produced 4.4 g of colorless crystals.

b) 9,9'-Spirobifluorene-2,2'-dicarbonyl chloride 2 g (5 mmol) of 9,9'-spirobifluorene-2,2'-dicarboxylic acid were refluxed with 20 ml of (freshly distilled) thionyl chloride and 3 drops of DMF for 4 h in a 100 ml flask fitted with a reflux condenser and drying tube. After cooling, the reflux condenser was exchanged for a distillation bridge, and excess thionyl chloride was distilled off under reduced pressure; 40 ml of petroleum ether (30°–60° C.) were added to the residue, which was distilled off to leave the crystalline acid chloride.

c) 2,2'-Bis[(5(p-t-butylphenyl)-1,3,4-oxadiazol-2yl]-9,9'-spirobifluorene 2.0 g (11 mmol) of 5(4-t-butylphenyl)tetrazole dissolved in 20 ml of anhydrous pyridine were added to the acid chloride, and the mixture was refluxed for 2 h under protective gas. After cooling, the mixture was introduced into 200 ml of water and left to stand for 2 h. The oxadiazole derivative which precipitated out was filtered off with suction, washed with water and dried under reduced pressure. It was then chromatographed over silica gel using chloroform/ethyl acetate (99:1), and recrystallized from chloroform/pentane. This gave 2.4 g of colorless crystals.

$^1$H-NMR (CDCl$_3$), ppm):

1.31 (s, 18H, t-butyl), 6.77 (d, J=7.32Hz, 2H), 7.18 (td, J=7.48, 1.22Hz, 2H), 7.44 (td, J=7.40, 1.22Hz, 2H), 7.46 (d, J=8.54Hz, 4H), 7.50 (d, J=1.22Hz, 2H), 7.94 (d, J=8.54Hz, 4H), 8.02 (d, J=7.93 Hz, 6H), 8.20 (dd, J=7.93, 1.53 Hz, 2H).

C. Application examples

Example 1

100 parts of polyester granules of ethylene glycol polyterephthalate were intimately mixed with 0.05 parts of the compound of the formula (A) and melted at 285° C. with stirring.

Spinning the spinning dope using customary spinnerets gave greatly brightened polyester fibers. The use of a compound of the formula (B) or (C) instead of the compound of the formula (A) produced similar results.

Example 2

A polyester fabric ("Dacron") was formulated at room temperature using an aqueous dispersion which comprised, per liter, 2 g of the compounds of the formula (B) and 1 g of an addition product of about 8 mol of ethylene oxide with 1 mol of p-tert-octylphenol, and dried at about 100° C. The dry material was then subjected briefly to a heat treatment at 220° C. The material treated in this way had a significantly whiter appearance than the untreated material.

The use of a compound of the formula (A) or (C) instead of the compound of the formula (B) produced similar results.

A:

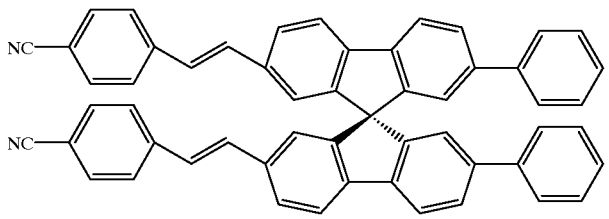

B:

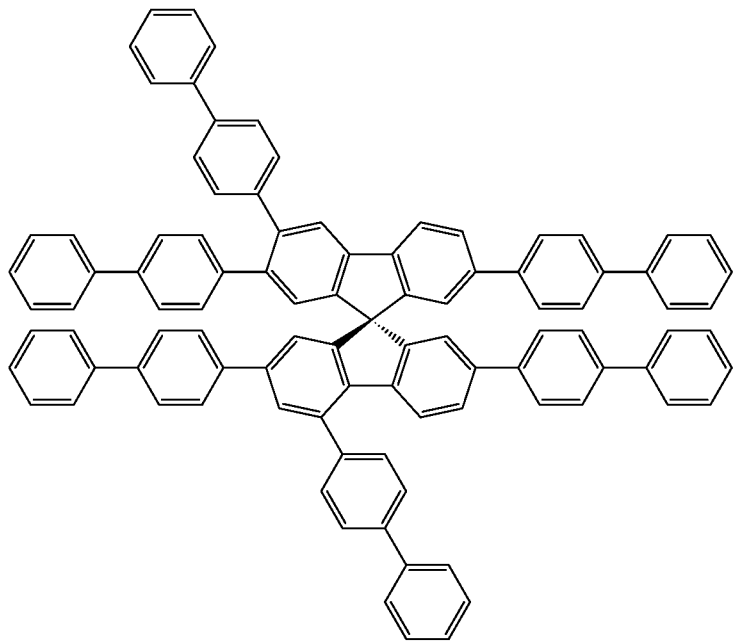

C:

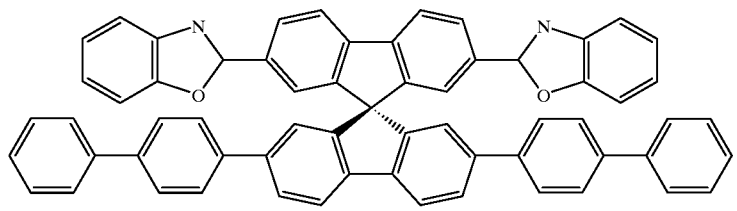

TABLE 1

Spectral data of selected optical brighteners

| Compound | Absorption λ$_{max}$ [nm] | Extinction lg ε | Emission λ$_{max}$ [nm] |
|---|---|---|---|
| 1 | 334 | 4.85 | 359, 378 |
| 2 | 342 | 5.11 | 385, 406 |
| 3 | 344 | 5.23 | 395, 416 |
| 4 | 344 |  | 405, 422 |
| 5 | 353 |  | 391, 412 |
| 6 | 363 |  | 392, 413 |
| 7 | 330 |  | 355, 373, 393 |

TABLE 2

Thermochemical data of selected spiro compounds

| Compound | Melting point [° C.] | Thermal degradation (5% weight loss) |
|---|---|---|
| 1 | 296 | 425 |
| 2 | 408 | 550 |
| 3 | 438 | 585 |
| 8 | 316 | 465 |
| 6 | 365 | 565 |
| 7 | 337 | — |

Cpd. 1: 2,2',7,7'-tetraphenyl-9,9'-spirobifluorene (Ex. 3)
Cpd. 2: 2,2',7,7'-tetrakis(biphenyl-4-yl)-9,9'-spirobifluorene (Ex. 4)
Cpd. 3: 2,2',7,7'-tetrakis(terphenyl-4-yl)-9,9'-spirobifluorene
Cpd. 4: 2,2',7,7'-tetrakis(quaterphenyl-4-yl)-9,9'-spirobifluorene
Cpd. 5: 2,2',7,7'-tetrakis(4'-methoxybiphenyl-4-yl)-9,9'-spirobifluorene
Cpd. 6: 2,2',4,4',7,7'-hexakis(biphenyl-4-yl)-9,9'-spirobifluorene TABLE 2-continued Thermochemical data of selected spiro compounds

| Compound | Melting point [° C.] | Thermal degradation (5% weight loss) |
|---|---|---|
| Cpd. 7: 2,2'-bis[(5(p-t-butylphenyl-1,3,4-oxadiazol-2-yl]-9,9'-spirobifluorene | | |
| Cpd. 8: 2,2',4,4',7,7'-hexaphenyl-9,9'-spirofluorene. | | |

What is claimed is:

1. A method of optically brightening which comprises adding to a material to be optically brightened one or more spiro compounds of the formula

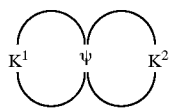
(I)

where

K¹ and K², which are identical or different, are conjugated systems, and ψ is C, Si, Ge, Sn or Pb.

2. The method as claimed in claim 1, wherein ψ is C or Si.

3. The method as claimed in claim 2, wherein ψ is C.

4. The method as claimed in claim 1, which comprises a spirofluorene of the formula (II),

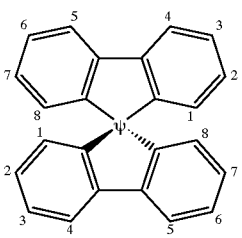
(II)

where ψ is C, Si, Ge, Sn or Pb, and the benzo groups, are independently of one another, can be substituted with an unsubstituted aryl or aryl substituted with an aromatic group(s) that can be substituted with alkyl groups and the aromatic groups optionally containing heteroatoms, and/or fused.

5. The method as claimed in claim 1, wherein the Spiro compounds are 2,2',4,4',7,7'-hexakis(biphenylyl)-9,9'-spirobifluorene;
2,2',4,4',7,7'-hexakis(terphenylyl)-9,9'-spirobifluorene;
2,2',4,4',7,7'-hexakis(quaterphenylyl)-9,9'-spirobifluorene; or
2,2',4,4',7,7'-hexakis(pentaphenylyl)-9,9'-spirobifluorene.

6. The method as claimed in claim 2, which comprises a spirobifluorene derivative of the formula (IIIa) to (IIIg):

IIIa) K=L=M=N and is a group of the formula:

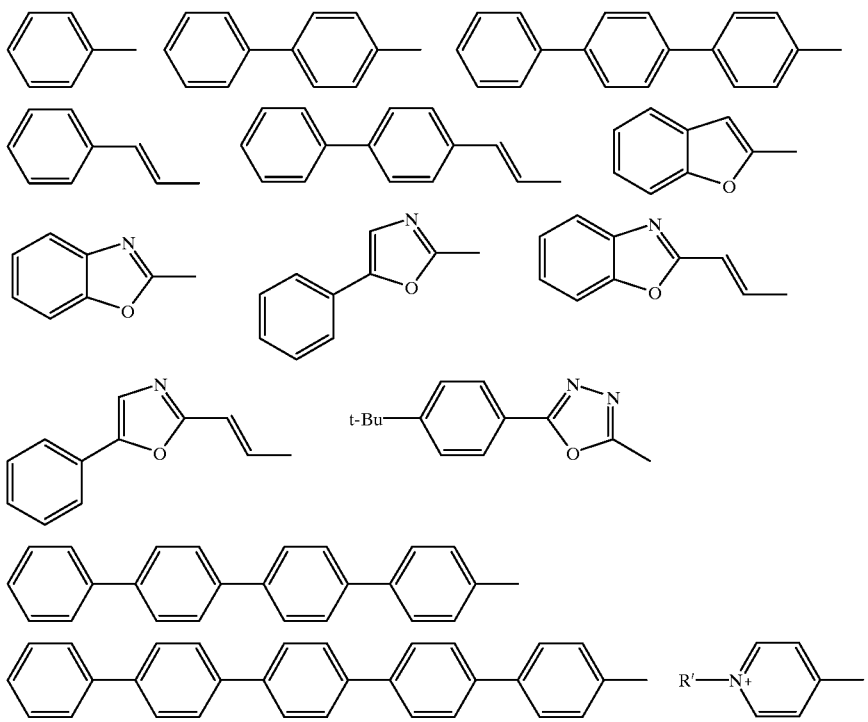

R'=C$_1$–C$_{22}$-Alkyl, C$_2$H$_4$SO$_3$—
IIIb) K=M=H and N=L and is a group of the formula:
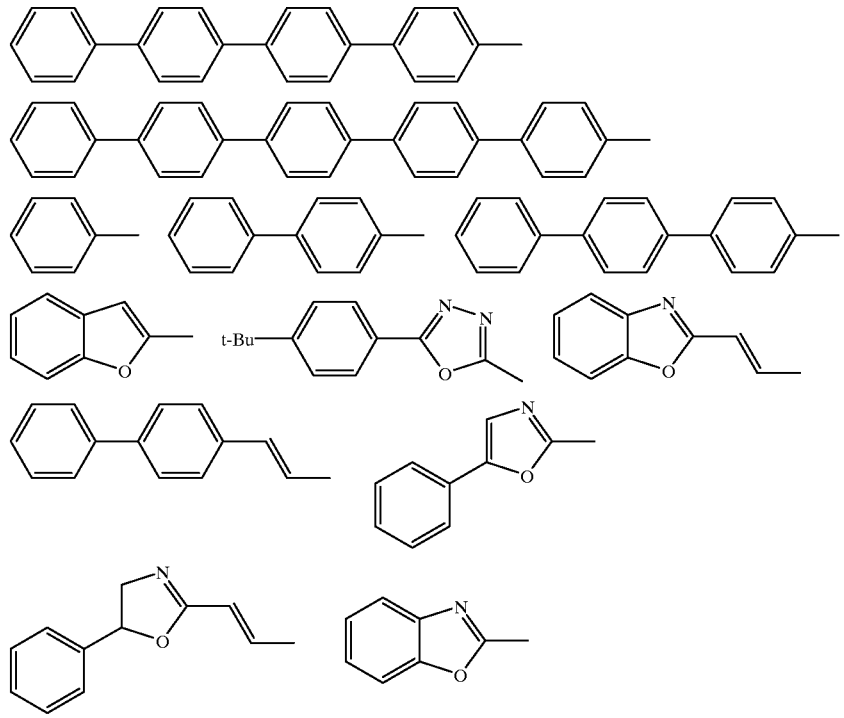
IIIc) K=M and is a group of the formula:
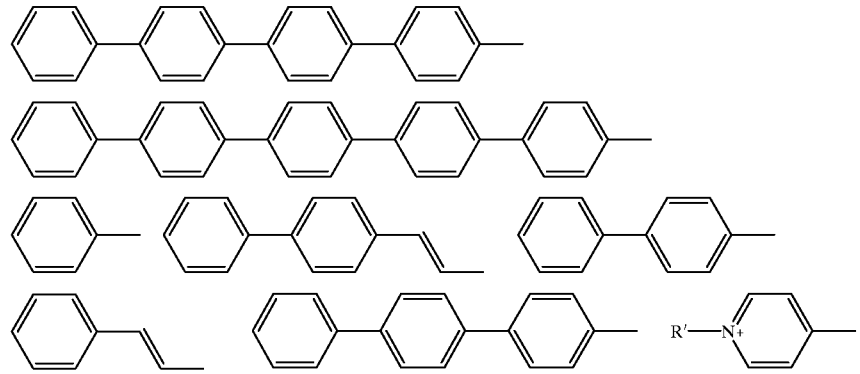
R'=C$_1$–C$_{22}$-Alkyl, C$_2$H$_4$SO$_3$—
and N=L and is a group of the formula:
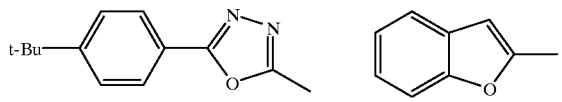

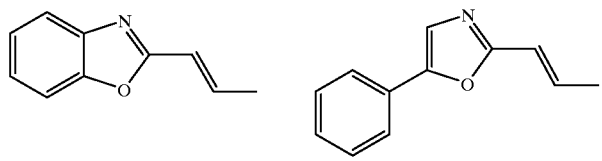
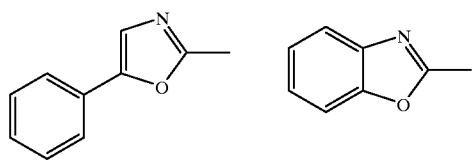
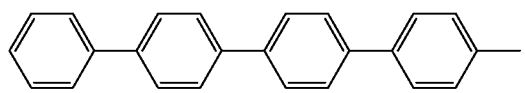
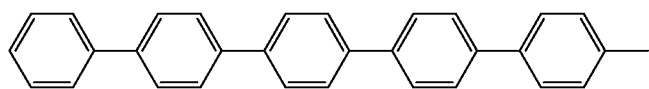
IIId) K=M and is a group of the formula:
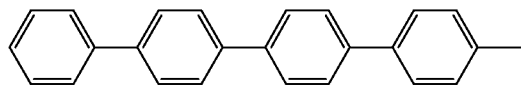
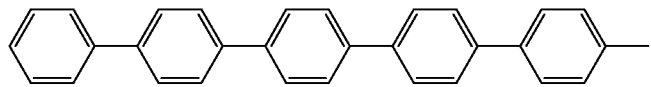
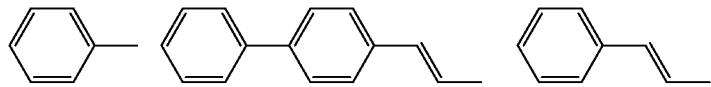
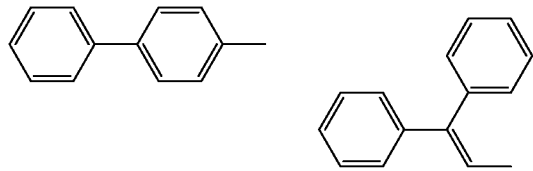
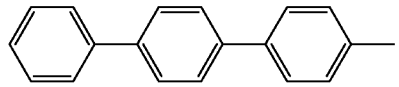

and N=L and is a group of the formula:
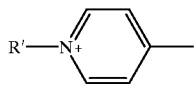
5
R'=$C_1$–$C_{22}$-Alkyl, $C_2H_4SO_3^-$
IIIe) K=L=H and M=N and is a group of the formula:
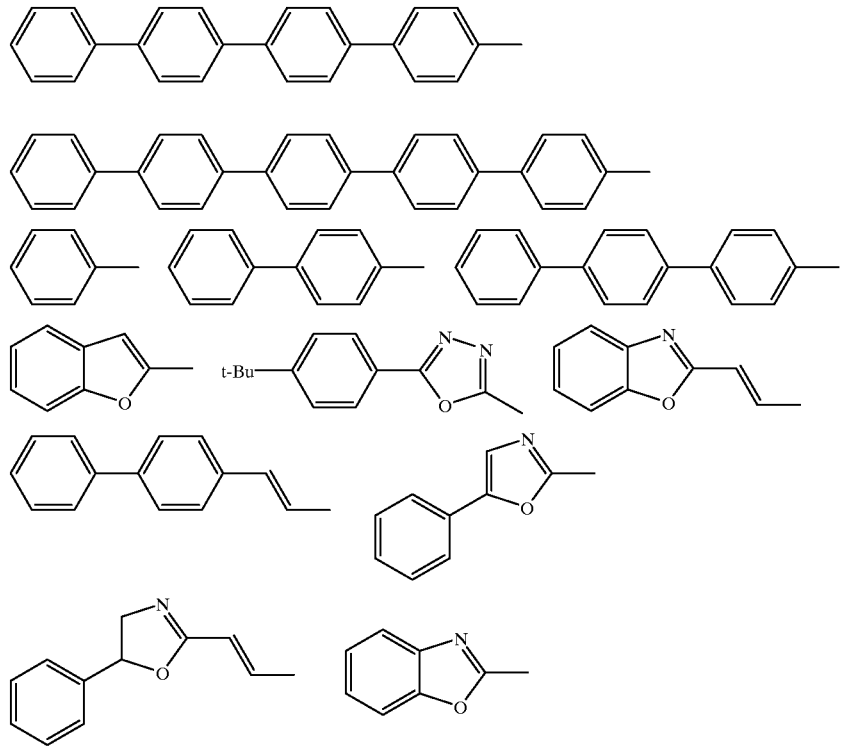
IIIf) K=M and is a group of the formula:
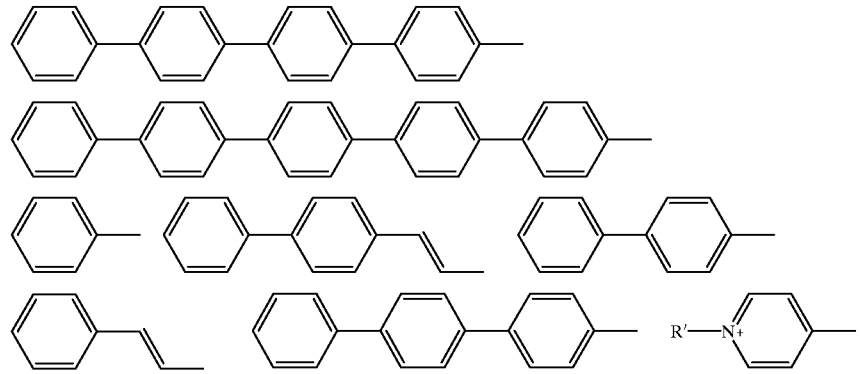

R'=$C_1$–$C_2$-Alkyl, $C_2H_4SO_3^-$
and M=N and is a group of the formula:
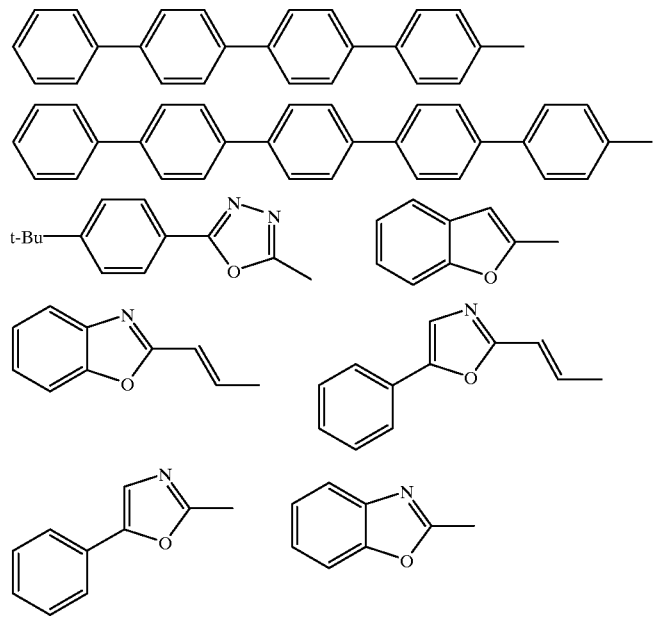
IIIg) K=L and is a group of the formula:
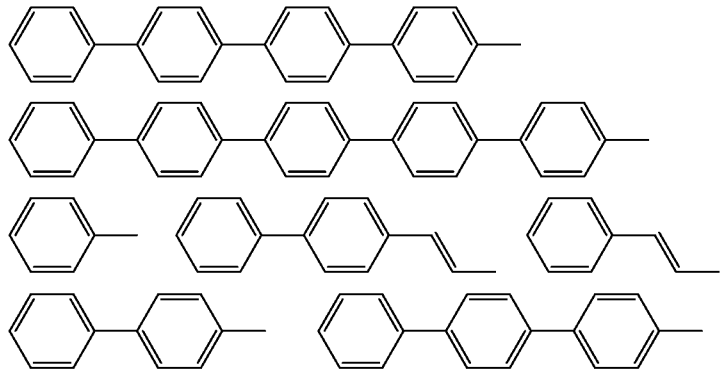
and M=N and is the group of the formula:
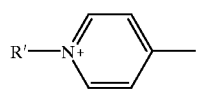
R'=$C_1$–$C_{22}$-Alkyl, $C_2H_4SO_3^-$.
7. The method thereof as claimed in claim 1, which comprises a spirobifluorene derivative of the formula (III),
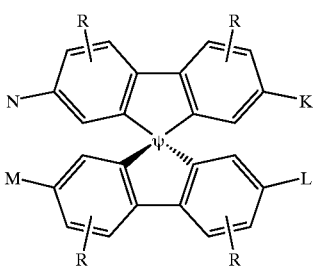
(III)
where K, L, M, N are identical or different and are a group of the following formulae:

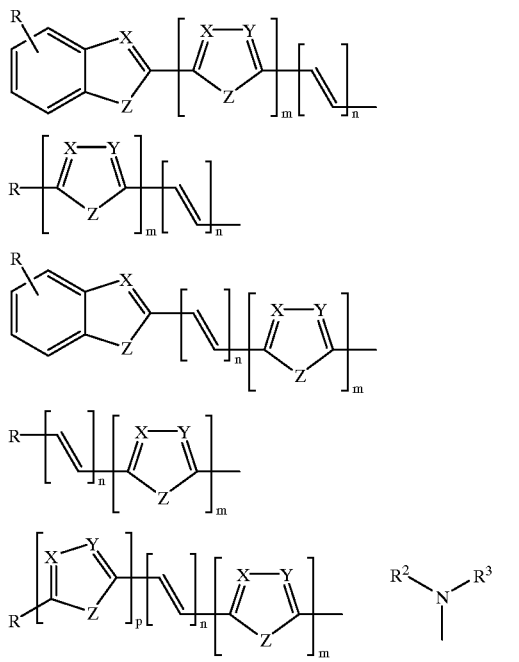

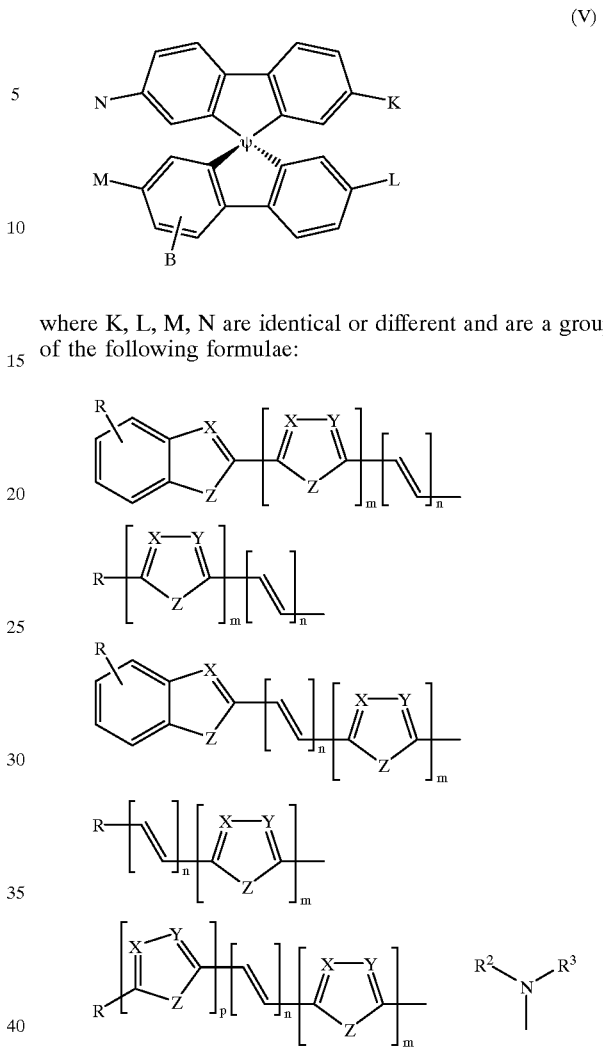

R is identical or different and is as defined for K, L, M, N or is —H, a linear or branched alkyl, alkoxy or carboalkoxy group having form 1 to 22 carbon atoms, —CN, —NO$_2$, —NR$^2$R$^3$, —N$^+$R$^2$R$^3$R$^4$, NOR$^2$R$^3$, —Ar or —O—Ar;

Ar is phenyl, biphenyl, 1-naphthyl, 2-naphthyl, 2-thienyl or 2-furanyl, where each of these groups optionally carry one or two radicals R, m, n and p are identical or different and are 0 1, 2, 3, 4 or 5;

X and Y are identical or different and are CR or N;

Z is —O—, —S—, —NR—, CR'R—, —CH=CH= or —CH=N—;

R$^1$ is as defined for R;

R$^2$, R$^3$ and R$^4$ are identical or different and are H, a linear or branched alkyl group having from 1 to 22 carbon atoms, —Ar or 3-methylphenyl.

8. An optical brightener which contains a material and
a. which has a fluoroescence quantum yield of ≧40% in solid form, and
b. an emission maximum in the range from 380 to 750 nm, measured at room temperature, decreases by no greater than 25%, relative to an initial state, after the material, applied in a thickness of no greater than 1 μm to a quartz substrate, has been heated to 250° C. in an inert atmosphere at a pressure no greater than 1 mbar for 30 min.

9. The optical brightener as claimed in claim 7, which has a fluorescence quantum yield in the solid of ≧50%.

10. The optical brightener as claimed in claim 9, wherein the emission maximum is in the range from 380 to 750 nm, measured at room temperature decreases by no greater than 20% relative to the initial state for thermal treatment.

11. The optical brightener as claimed in claim 10, wherein the emission maximum is no greater than 15% relative to the initial state before thermal treatment and the fluorescence quantum yield of ≧60%.

12. The optical brightener as claimed in claim 8, wherein the material is a Spiro compound of formula (V)

where K, L, M, N are identical or different and are a group of the following formulae:

R is identical or different and is as defined for K, L, M, N or is —H, a linear or branched alkyl, alkoxy or carboalkoxy group having form 1 to 22 carbon atoms, —CN, —NO$_2$, —NR$^2$R$^3$, —N$^+$R$^2$R$^3$R$^4$, NOR$^2$R$^3$, —Ar or —O—Ar;

Ar is phenyl, biphenyl, 1-naphthyl, 2-naphthyl, 2-thienyl or2-furanyl, where each of these groups optionally carry one or two radicals R;

m, n and p are identical or different and are 0, 1, 2, 3, 4 or 5;

X and Y are identical or different and are CR or N;

Z is —O—, —S—, —NR—, CR$^1$R—, —CH=CH= or —CH=N—:

R$^1$ is as defined for R;

R$^2$, R$^3$ and R$^4$ are identical or different and are H, a linear or branched alkyl group having from 1 to 22 carbon atoms, —Ar or 3-methylphenyl.

13. The optical brightener as claimed in claim 12 wherein R is identical or different and is hydrogen, a linear or branched alkyl, alkoxy, carboalkoxy group having from 1 to 12 carbon atoms, —SO$_2$CH$_3$, —CF$_3$, halogen, —SO$_3$H, —SO$_2$Na(K), —PO(OC$_2$H$_5$)$_2$, —CH$_3$OSO$_3$—, —N(CH$_3$)$_3^+$, or —O—(CH$_2$)$_2$— N$^+$(CH$_3$)(CH$_2$H$_5$)$_2$ and n is 0.

* * * * *